United States Patent
Lethé et al.

(10) Patent No.: US 7,563,870 B2
(45) Date of Patent: Jul. 21, 2009

(54) LAGE-1 TUMOR ASSOCIATED NUCLEIC ACIDS

(75) Inventors: Bernard Lethé, Brussels (BE); Sophie Lucas, Brussels (BE); Charles De Smet, Brussels (BE); Daniele Godelaine, Brussels (BE); Thierry Boon-Falleur, Brussels (BE)

(73) Assignee: Ludwig Institute for Cancer Research Ltd., New York, NY (US)

( * ) Notice: Subject to any disclaimer, the term of this patent is extended or adjusted under 35 U.S.C. 154(b) by 287 days.

(21) Appl. No.: 10/877,373

(22) Filed: Jun. 25, 2004

(65) Prior Publication Data

US 2004/0234541 A1 Nov. 25, 2004

Related U.S. Application Data

(60) Division of application No. 09/341,829, filed as application No. PCT/US98/01445 on Jan. 27, 1998, now Pat. No. 6,794,131, application No. 10/877,373, which is a continuation-in-part of application No. 08/791,495, filed on Jan. 27, 1997, now abandoned.

(51) Int. Cl.
C07K 14/00 (2006.01)
(52) U.S. Cl. ............... 530/350; 530/300; 424/184.1
(58) Field of Classification Search ........... 530/350, 530/300; 424/184.1
See application file for complete search history.

(56) References Cited

U.S. PATENT DOCUMENTS

| | | | |
|---|---|---|---|
| 5,342,774 A | 8/1994 | Boon et al. | |
| 5,405,940 A | 4/1995 | Boon et al. | |
| 5,804,381 A * | 9/1998 | Chen et al. | 435/6 |
| 6,140,050 A | 10/2000 | Sahin et al. | |
| 6,251,603 B1 | 6/2001 | Jäger et al. | |
| 6,252,052 B1 | 6/2001 | Stockert et al. | |
| 6,274,145 B1 | 8/2001 | Chen et al. | |
| 6,338,947 B1 | 1/2002 | Sahin et al. | |
| 6,417,165 B1 | 7/2002 | Valmori et al. | |
| 6,525,177 B2 * | 2/2003 | Stockert et al. | 530/350 |
| 6,605,711 B1 | 8/2003 | Valmori et al. | |
| 6,689,742 B1 | 2/2004 | Cerundolo et al. | |
| 7,084,239 B1 * | 8/2006 | Wang et al. | 530/300 |

FOREIGN PATENT DOCUMENTS

| | | |
|---|---|---|
| CA | 2346942 A1 | 4/2000 |
| EP | 1001022 A1 | 5/2000 |
| EP | 1121435 A1 | 8/2001 |
| WO | 96/10577 | 4/1996 |
| WO | 98/14464 | 4/1998 |
| WO | 0023584 A1 | 4/2000 |

OTHER PUBLICATIONS

Greenbaum et al. (Genome Biology, 2003, vol. 4, Issue 9, pp. 117.1-117.8).*
Fu et al 1996 (EMBO Journal, vol. 15, pp. 4392-4401).*
Yokota, J et al, 1988 (Oncogene, vol. 3, pp. 471-475).*
Zimmer, 1991 (Cell Motility and the Cytoskeleton, vol. 20, pp. 325-337).*
Guo et al, 2002 (Journal of Pharmacology and Experimental Therapeutics, vol. 300, pp. 206-212).*
White et al, 2001 (Ann Rev Med, 52: 125-145).*
Boon, 1992 (Adv Can Res, 58:177-210).*
Smith RT, 1994 (Clin Immunol, 41(4):841-849).*
Kirkin et al, 1998, APMIS, 106 : 665-679.*
MPSRCH search report, 2006, us10.877.373.5rai, pp. 11-12.*
Hell et al, 1995 (Laboratory Investigation, vol. 73, pp. 492-496).*
MPSRCH search result, 2006, us-10-877-373-5.Oligo.rpr, result 11, pp. 1-2.*
MPSRCH search report, 2008, US-10-877-373-5.rai. result 15, pp. 1-2.*
MPSRCH search result, 2008, us-10-877-373-5.oligo.rai, result 9, p. 1.*
Sharma P. et al., "Frequency of NY-ESO-1 and LAGE-1 expression in bladder cancer and evidence of a new NY-ESO-1 T-cell epitope in a patient with bladder cancer," *Cancer Immun.*, Dec. 18, 2003; 3:19.
Odunsi K. et al., "NY-ESO-1 and LAGE-1 cancer-testis antigens are potential targets for immunotherapy in epithelial ovarian cancer," *Cancer Res.*, Sep. 15, 2003; 63(18):6076-83.
Usener D. et al., "Seroreactivity against MAGE-A and LAGE-1 proteins in melanoma patients." *Br J Dermatol.*, Aug. 2003; 149(2):282-8.
Slager E.H. et al., "CD4+ Th2 cell recognition of HLA-DR-restricted epitopes derived from CAMEL: a tumor antigen translated in an alternative open reading frame," *J Immunol.*, Feb. 1, 2003; 170(3):1490-7.
Rimoldi D. et al., "Efficient simultaneous presentation of NY-ESO-1/LAGE-1 primary and nonprimary open reading frame-derived CTL epitopes in melanoma," *J Immunol.*, Dec. 15, 2000; 165(12):7253-61.
Mandic M. et al. "The alternative open reading frame of LAGE-1 gives rise to multiple promiscuous HLA-DR-restricted epitopes recognized by T-helper 1-type tumor-reactive CD4+ T cells," *Cancer Res.*, Oct. 1, 2003; 63(19):6506-15.
Aarnoudse C.A., "Interleukin-2-induced, melanoma-specific T cells recognize CAMEL, an unexpected translation product of LAGE-1," *Int J Cancer.*, Jul. 30, 1999; 30;82(3):442-8.

(Continued)

*Primary Examiner*—Larry R. Helms
*Assistant Examiner*—Minh-Tam Davis
(74) *Attorney, Agent, or Firm*—Wolf, Greenfield & Sacks, P.C.

(57) ABSTRACT

The invention describes the LAGE-1 tumor associated gene, including fragments, allelic variants and splice variants thereof. Also included are polypeptides and fragments thereof encoded by such genes, and antibodies relating thereto. Methods and products also are provided for diagnosing and treating conditions characterized by expression of a LAGE-1 gene product.

6 Claims, 1 Drawing Sheet

OTHER PUBLICATIONS

Lethe B. et al, "LAGE-1, a new gene with tumor specificity," *Int J Cancer.*, Jun. 10, 1998; 76(6):903-8.
Ausubel, FM et al, eds, 1987, Current protocols in molecular biology, John Wiley & Sons, New York, pages 6.3.5.
Yokota, J et al. Oncogene, 1988, vol. 3, pp. 471-475.
Jansen, M. et al, 1995, Pediatric Res, 37 (6):681-686.
Sambook et al, eds, 1989, Molecular cloning, a Laboratory manual, Cold Spring Harbor Laboratory Press, Cold Sprin Harbor, p. 14.2-14.4.
Bowie et al. (Science, 190, 257: 1306-1310).
Burgess et al. (J. of Cell Biol. 111:2129-2138, 1990).
Lazar et al (Molecular and Cellular Biology, 1988, 8:1247-1252).
Bork (Genome Research, 2000, 10:398-400).
Scott et al (Nature Genetics, 1999, 21:440-443).
Miller (1995, FASEB J., vol. 9, pp. 190-199).
Deonarain (1998, Expert Opin. Ther. Pat., vol. 8, pp. 53-69).
Verma (Sep. 1997, Nature, vol. 389,-242).
Crystal (1995, Science, vol. 270, p. 404-410).
Ezzel, J. NIH Res. 7:46-49, 1995.
Spitler, Cancer Biotherapy 10:1-3, 1995.
Boon, Adv. Cancer Res. 58: 177-210, 1992.
Burgess, J. Cell Biol. 11:2129-2138, 1990.
Lazar, Mol. Cell. Biol. 8: 1247-1252, 1988.
Toa, Immunol. 143 (8):2595-2601, 1989.
Gillies, Juman Antibod. Hybridomas 1(1): 47-54, 1990.
Shantz, LM., Intl. J. Biochem Cell Biol. 31:107-122, 1999.
Fu et al. EMBOJ 15 (16): 4392-4401, 1996.
Hubert, The Dict. Immunol. AP, $4^{th}$ ed., p. 55, 1995.
Greenspan. Nature Biotech. 7: 936-937, 1999.
Reigrer-Glossary of Genetics Cytogenetics, Classical Mol.$4^{th}$ ed., Springer-Verlay Berlin, p. 17, 1976.
Alberts et al. Mol Bio. Cell, $3^{rd}$ ed. p. 465, 1994.
McClean. Eur. J. Cancer 29A: 2243-2248, 1993.
Chen, et al., "A testicular antigen aberrantly expressed in human cancers detected by autologous antibody screening," Proc. Nat'l. Acad. Sci. USA vol. 94 pp. 1914-1918 (Mar. 1997).
Hillier, EMBL Database, Accession No. AA634317 (Oct. 1997).
Traversari, et al., Immunogenetics 35:145 (1992).
Van der Bruggen, et al. Science 254:1643-1647 (1991).
Rammensee, et al., Immunogenetics 41:178-228 (1995).
Van den Eynde, et al., Curr. Opinion in Immun. 7:674-681 (1995).
De Plaen et al., Immunogenetics 40:360-369, (1994).
Coulie et al., Stem Cells 13:393-403, (1995).
Hubank and Schatz, Nucl. Acids Res. 22:5640, (1994).

\* cited by examiner

SEQUENCE LISTING

<160> NUMBER OF SEQ ID NOS: 14

<210> SEQ ID NO 1
<211> LENGTH: 217
<212> TYPE: DNA
<213> ORGANISM: Homo sapiens

```
<400> SEQUENCE: 1
gatctcagaa cacccaaaca caaggtctca gaacagagac ctggtacacc aggcccgccg      60
ccacccgagg gagcccaggg agatgggtgc agaggtgtcg cctttaatgt gatgttctct     120
gcccctcaca tttagccgac tgactgctgc agaccaccgc caactgcagc tctccatcag     180
ctcctgtctc cagcagcttt ccctgttgat gtggatc                              217

<210> SEQ ID NO 2
<211> LENGTH: 18
<212> TYPE: DNA
<213> ORGANISM: Homo sapiens

<400> SEQUENCE: 2
agatgggtgc agaggtgt                                                    18

<210> SEQ ID NO 3
<211> LENGTH: 19
<212> TYPE: DNA
<213> ORGANISM: Homo sapiens

<400> SEQUENCE: 3
gatccacatc aacagggaa                                                   19

<210> SEQ ID NO 4
<211> LENGTH: 1002
<212> TYPE: DNA
<213> ORGANISM: Homo sapiens
<220> FEATURE:
<221> NAME/KEY: CDS
<222> LOCATION: (65)..(697)

<400> SEQUENCE: 4
tctgcctccg catcctcgtg ggccctgacc ttctctctga gagccgggca gaggctccgg      60 agcc atg cag gcc gaa ggc cag ggc aca ggg ggt tcg acg ggc gat gct     109
     Met Gln Ala Glu Gly Gln Gly Thr Gly Gly Ser Thr Gly Asp Ala
      1               5                  10                  15 gat ggc cca gga ggc cct ggc att cct gat ggc cca ggg ggc aat gct     157
Asp Gly Pro Gly Gly Pro Gly Ile Pro Asp Gly Pro Gly Gly Asn Ala
             20                  25                  30 ggc ggc cca gga gag gcg ggt gcc acg ggc ggc aga ggt ccc cgg ggc     205
Gly Gly Pro Gly Glu Ala Gly Ala Thr Gly Gly Arg Gly Pro Arg Gly
         35                  40                  45 gca ggg gca gca agg gcc tcg ggg ccg aga gga ggc gcc ccg cgg ggt     253
Ala Gly Ala Ala Arg Ala Ser Gly Pro Arg Gly Gly Ala Pro Arg Gly
     50                  55                  60 ccg cat ggc ggt gcc gct tct gcg cag gat gga agg tgc ccc tgc ggg     301
Pro His Gly Gly Ala Ala Ser Ala Gln Asp Gly Arg Cys Pro Cys Gly
 65                  70                  75 gcc agg agg ccg gac agc cgc ctg ctt cag ttg cac atc acg atg cct     349
Ala Arg Arg Pro Asp Ser Arg Leu Leu Gln Leu His Ile Thr Met Pro
 80                  85                  90                  95 ttc tcg tcg ccc atg gaa gcg gag ctg gtc cgc agg atc ctg tcc cgg     397
Phe Ser Ser Pro Met Glu Ala Glu Leu Val Arg Arg Ile Leu Ser Arg
                100                 105                 110 gat gcc gca cct ctc ccc cga cca ggg gcg gtt ctg aag gac ttc acc     445
Asp Ala Ala Pro Leu Pro Arg Pro Gly Ala Val Leu Lys Asp Phe Thr
            115                 120                 125 gtg tcc ggc aac cta ctg ttt atg tca gtt cgg gac cag gac agg gaa     493
Val Ser Gly Asn Leu Leu Phe Met Ser Val Arg Asp Gln Asp Arg Glu
        130                 135                 140
```

| | | |
|---|---|---|
| ggc gct ggg cgg atg agg gtg gtg ggt tgg ggg ctg gga tcc gcc tcc<br>Gly Ala Gly Arg Met Arg Val Val Gly Trp Gly Leu Gly Ser Ala Ser<br>145                    150                    155 | | 541 |
| ccg gag ggg cag aaa gct aga gat ctc aga aca ccc aaa cac aag gtc<br>Pro Glu Gly Gln Lys Ala Arg Asp Leu Arg Thr Pro Lys His Lys Val<br>160                    165                    170                    175 | | 589 |
| tca gaa cag aga cct ggt aca cca ggc ccg ccg cca ccc gag gga gcc<br>Ser Glu Gln Arg Pro Gly Thr Pro Gly Pro Pro Pro Pro Glu Gly Ala<br>                    180                    185                    190 | | 637 |
| cag gga gat ggg tgc aga ggt gtc gcc ttt aat gtg atg ttc tct gcc<br>Gln Gly Asp Gly Cys Arg Gly Val Ala Phe Asn Val Met Phe Ser Ala<br>                    195                    200                    205 | | 685 |
| cct cac att tagccgactg actgctgcag accaccgcca actgcagctc<br>Pro His Ile<br>          210 | | 734 |
| tccatcagct cctgtctcca gcagctttcc ctgttgatgt ggatcacgca gtgctttctg | | 794 |
| cccgtgtttt tggctcaggc tccctcaggg cagaggcgct aagcccagcc tggcgcccct | | 854 |
| tcctaggtca tgcctcctcc cctagggaat ggtcccagca cgagtggcca gttcattgtg | | 914 |
| ggggcctgat tgtttgtcgc tgaggagga cggcttacat gtttgtttct gtagaaaata | | 974 |
| aagctgagct acgattccga aaaaaaaa | | 1002 |

<210> SEQ ID NO 5
<211> LENGTH: 210
<212> TYPE: PRT
<213> ORGANISM: Homo sapiens

<400> SEQUENCE: 5

Met Gln Ala Glu Gly Gln Gly Thr Gly Gly Ser Thr Gly Asp Ala Asp
1                  5                    10                    15

Gly Pro Gly Gly Pro Gly Ile Pro Asp Gly Pro Gly Gly Asn Ala Gly
                  20                    25                    30

Gly Pro Gly Glu Ala Gly Ala Thr Gly Gly Arg Gly Pro Arg Gly Ala
                  35                    40                    45

Gly Ala Ala Arg Ala Ser Gly Pro Arg Gly Gly Ala Pro Arg Gly Pro
      50                    55                    60

His Gly Gly Ala Ala Ser Ala Gln Asp Gly Arg Cys Pro Cys Gly Ala
65                  70                    75                    80

Arg Arg Pro Asp Ser Arg Leu Leu Gln Leu His Ile Thr Met Pro Phe
                        85                    90                    95

Ser Ser Pro Met Glu Ala Glu Leu Val Arg Arg Ile Leu Ser Arg Asp
                100                    105                    110

Ala Ala Pro Leu Pro Arg Pro Gly Ala Val Leu Lys Asp Phe Thr Val
                115                    120                    125

Ser Gly Asn Leu Leu Phe Met Ser Val Arg Asp Gln Asp Arg Glu Gly
      130                    135                    140

Ala Gly Arg Met Arg Val Val Gly Trp Gly Leu Gly Ser Ala Ser Pro
145                  150                    155                    160

Glu Gly Gln Lys Ala Arg Asp Leu Arg Thr Pro Lys His Lys Val Ser
                165                    170                    175

Glu Gln Arg Pro Gly Thr Pro Gly Pro Pro Pro Pro Glu Gly Ala Gln
                  180                    185                    190

Gly Asp Gly Cys Arg Gly Val Ala Phe Asn Val Met Phe Ser Ala Pro
                195                    200                    205

His Ile
      210

<210> SEQ ID NO 6
<211> LENGTH: 632
<212> TYPE: DNA
<213> ORGANISM: Homo sapiens
<220> FEATURE:
<221> NAME/KEY: CDS
<222> LOCATION: (53)...(595)

<400> SEQUENCE: 6

```
tcctcgtggg ccctgacctt ctctctgaga gccgggcaga ggctccggag cc atg            55
                                                          Met
                                                           1 cag gcc gaa ggc cag ggc aca ggg ggt tcg acg ggc gat gct gat ggc         103
Gln Ala Glu Gly Gln Gly Thr Gly Gly Ser Thr Gly Asp Ala Asp Gly
         5                  10                  15 cca gga ggc cct ggc att cct gat ggc cca ggg ggc aat gct ggc ggc         151
Pro Gly Gly Pro Gly Ile Pro Asp Gly Pro Gly Gly Asn Ala Gly Gly
     20                  25                  30 cca gga gag gcg ggt gcc acg ggc ggc aga ggt ccc cgg ggc gca ggg         199
Pro Gly Glu Ala Gly Ala Thr Gly Gly Arg Gly Pro Arg Gly Ala Gly
 35                  40                  45 gca gca agg gcc tcg ggg ccg aga gga ggc gcc ccg cgg ggt ccg cat         247
Ala Ala Arg Ala Ser Gly Pro Arg Gly Gly Ala Pro Arg Gly Pro His
 50                  55                  60                  65 ggc ggt gcc gct tct gcg cag gat gga agg tgc ccc tgc ggg gcc agg         295
Gly Gly Ala Ala Ser Ala Gln Asp Gly Arg Cys Pro Cys Gly Ala Arg
                 70                  75                  80 agg ccg gac agc cgc ctg ctt cag ttg cac atc acg atg cct ttc tcg         343
Arg Pro Asp Ser Arg Leu Leu Gln Leu His Ile Thr Met Pro Phe Ser
             85                  90                  95 tcg ccc atg gaa gcg gag ctg gtc cgc agg atc ctg tcc cgg gat gcc         391
Ser Pro Met Glu Ala Glu Leu Val Arg Arg Ile Leu Ser Arg Asp Ala
        100                 105                 110 gca cct ctc ccc cga cca ggg gcg gtt ctg aag gac ttc acc gtg tcc         439
Ala Pro Leu Pro Arg Pro Gly Ala Val Leu Lys Asp Phe Thr Val Ser
    115                 120                 125 ggc aac cta ctg ttt atc cga ctg act gct gca gac cac cgc caa ctg         487
Gly Asn Leu Leu Phe Ile Arg Leu Thr Ala Ala Asp His Arg Gln Leu
130                 135                 140                 145 cag ctc tcc atc agc tcc tgt ctc cag cag ctt tcc ctg ttg atg tgg         535
Gln Leu Ser Ile Ser Ser Cys Leu Gln Gln Leu Ser Leu Leu Met Trp
                150                 155                 160 atc acg cag tgc ttt ctg ccc gtg ttt ttg gct cag gct ccc tca ggg         583
Ile Thr Gln Cys Phe Leu Pro Val Phe Leu Ala Gln Ala Pro Ser Gly
            165                 170                 175 cag agg cgc taagcccagc ctggcgcccc ttcctaggtc atgcctcctc                 632
Gln Arg Arg
        180
```

<210> SEQ ID NO 7
<211> LENGTH: 180
<212> TYPE: PRT
<213> ORGANISM: Homo sapiens

<400> SEQUENCE: 7

```
Met Gln Ala Glu Gly Gln Gly Thr Gly Gly Ser Thr Gly Asp Ala Asp
 1               5                  10                  15

Gly Pro Gly Gly Pro Gly Ile Pro Asp Gly Pro Gly Gly Asn Ala Gly
             20                  25                  30

Gly Pro Gly Glu Ala Gly Ala Thr Gly Gly Arg Gly Pro Arg Gly Ala
         35                  40                  45
```

-continued

```
Gly Ala Ala Arg Ala Ser Gly Pro Arg Gly Gly Ala Pro Arg Gly Pro
 50                  55                  60
His Gly Gly Ala Ala Ser Ala Gln Asp Gly Arg Cys Pro Cys Gly Ala
 65                  70                  75                  80
Arg Arg Pro Asp Ser Arg Leu Leu Gln Leu His Ile Thr Met Pro Phe
                 85                  90                  95
Ser Ser Pro Met Glu Ala Glu Leu Val Arg Arg Ile Leu Ser Arg Asp
                100                 105                 110
Ala Ala Pro Leu Pro Arg Pro Gly Ala Val Leu Lys Asp Phe Thr Val
            115                 120                 125
Ser Gly Asn Leu Leu Phe Ile Arg Leu Thr Ala Ala Asp His Arg Gln
130                 135                 140
Leu Gln Leu Ser Ile Ser Ser Cys Leu Gln Gln Leu Ser Leu Leu Met
145                 150                 155                 160
Trp Ile Thr Gln Cys Phe Leu Pro Val Phe Leu Ala Gln Ala Pro Ser
                165                 170                 175
Gly Gln Arg Arg
            180

<210> SEQ ID NO 8
<211> LENGTH: 755
<212> TYPE: DNA
<213> ORGANISM: Homo sapiens
<220> FEATURE:
<221> NAME/KEY: CDS
<222> LOCATION: (51)..(593)

<400> SEQUENCE: 8
ctcgtgggcc ctgaccttct ctctgagagc cgggcagagg ctccggagcc atg cag         56
                                                         Met Gln
                                                           1 gcc gaa ggc cgg ggc aca ggg ggt tcg acg ggc gat gct gat ggc cca       104
Ala Glu Gly Arg Gly Thr Gly Gly Ser Thr Gly Asp Ala Asp Gly Pro
      5                  10                  15 gga ggc cct ggc att cct gat ggc cca ggg ggc aat gct ggc ggc cca       152
Gly Gly Pro Gly Ile Pro Asp Gly Pro Gly Gly Asn Ala Gly Gly Pro
 20                  25                  30 gga gag gcg ggt gcc acg ggc ggc aga ggt ccc cgg ggc gca ggg gca       200
Gly Glu Ala Gly Ala Thr Gly Gly Arg Gly Pro Arg Gly Ala Gly Ala
 35                  40                  45                  50 gca agg gcc tcg ggg ccg gga gga ggc gcc ccg cgg ggt ccg cat ggc       248
Ala Arg Ala Ser Gly Pro Gly Gly Gly Ala Pro Arg Gly Pro His Gly
                 55                  60                  65 ggc gcg gct tca ggg ctg aat gga tgc tgc aga tgc ggg gcc agg ggg       296
Gly Ala Ala Ser Gly Leu Asn Gly Cys Cys Arg Cys Gly Ala Arg Gly
             70                  75                  80 ccg gag agc cgc ctg ctt gag ttc tac ctc gcc atg cct ttc gcg aca       344
Pro Glu Ser Arg Leu Leu Glu Phe Tyr Leu Ala Met Pro Phe Ala Thr
         85                  90                  95 ccc atg gaa gca gag ctg gcc cgc agg agc ctg gcc cag gat gcc cca       392
Pro Met Glu Ala Glu Leu Ala Arg Arg Ser Leu Ala Gln Asp Ala Pro
    100                 105                 110 ccg ctt ccc gtg cca ggg gtg ctt ctg aag gag ttc act gtg tcc ggc       440
Pro Leu Pro Val Pro Gly Val Leu Leu Lys Glu Phe Thr Val Ser Gly
115                 120                 125                 130 aac ata ctg act atc cga ctg act gct gca gac cac cgc caa ctg cag       488
Asn Ile Leu Thr Ile Arg Leu Thr Ala Ala Asp His Arg Gln Leu Gln
                135                 140                 145
```

```
ctc tcc atc agc tcc tgt ctc cag cag ctt tcc ctg ttg atg tgg atc      536
Leu Ser Ile Ser Ser Cys Leu Gln Gln Leu Ser Leu Leu Met Trp Ile
            150                 155                 160 acg cag tgc ttt ctg ccc gtg ttt ttg gct cag cct ccc tca ggg cag      584
Thr Gln Cys Phe Leu Pro Val Phe Leu Ala Gln Pro Pro Ser Gly Gln
        165                 170                 175 agg cgc taagcccagc ctggcgcccc ttcctaggtc atgcctcctc ccctagggaa        640
Arg Arg
    180 tggtcccagc acgagtggcc agttcattgt gggggcctga ttgtttgtcg ctggaggagg    700 acggcttaca tgtttgtttc tgtagaaaat aaaactgagc tacgaaaaaa aaaaa         755

<210> SEQ ID NO 9
<211> LENGTH: 180
<212> TYPE: PRT
<213> ORGANISM: Homo sapiens

<400> SEQUENCE: 9

Met Gln Ala Glu Gly Arg Gly Thr Gly Gly Ser Thr Gly Asp Ala Asp
 1               5                  10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
        180

<210> SEQ ID NO 10
<211> LENGTH: 18
<212> TYPE: DNA
<213> ORGANISM: Homo sapiens

<400> SEQUENCE: 10
gccatgcagg ccgaaggc                                                   18

<210> SEQ ID NO 11
<211> LENGTH: 19
<212> TYPE: DNA
<213> ORGANISM: Homo sapiens

<400> SEQUENCE: 11
ctggccactc gtgctggga                                                  19
```

-continued

```
<210> SEQ ID NO 12
<211> LENGTH: 18
<212> TYPE: DNA
<213> ORGANISM: Homo sapiens

<400> SEQUENCE: 12
gcaggatgga aggtgccc                                                 18

<210> SEQ ID NO 13
<211> LENGTH: 17
<212> TYPE: DNA
<213> ORGANISM: Homo sapiens

<400> SEQUENCE: 13
ccccaccgct tcccgtg                                                  17

<210> SEQ ID NO 14
<211> LENGTH: 20
<212> TYPE: DNA
<213> ORGANISM: Homo sapiens

<400> SEQUENCE: 14
ggctgaatgg atgctgcaga                                               20
```

LAGE-1 TUMOR ASSOCIATED NUCLEIC ACIDS

RELATED APPLICATIONS

This application is a divisional of U.S. patent application Ser. No. 09/341,829, filed Oct. 18, 1999, now issued as U.S. Pat. No. 6,794,131, which is a national stage filing under 35 U.S.C. § 371 of PCT International application PCT/US98/01445, filed Jan. 27, 1998, and published under PCT Article 21(2) in English, which is a continuation-in part of and claims priority under 35 U.S.C. § 120 from U.S. patent application Ser. No. 08/791,495, now abandoned, filed Jan. 27, 1997, each of which is incorporated by reference herein in its entirety.

FIELD OF THE INVENTION

This invention relates to nucleic acid molecules and encoded polypeptides which are expressed preferentially in tumors. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor associated" genes. These tumor associated genes are markers for the tumor phenotype. The expression of tumor associated genes can also be an essential event in the process of tumorigenesis.

Typically, the host recognizes as foreign the tumor associated genes which are not expressed in normal non-tumorigenic cells. Thus, the expression of tumor associated genes can provoke an immune response against the tumor cells by the host. Tumor associated genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis The discovery of tumor associated expression of a gene provides a means of identifying a cell as a tumor cell. Diagnostic compounds can be based on the tumor associated gene, and used to determine the presence and location of tumor cells. Further, when the tumor associated gene is essential for an aspect of the tumor phenotype (e.g., unregulated growth or metastasis), the tumor associated gene can be used to provide therapeutics such as antisense nucleic acids which can reduce or substantially eliminate expression of that gene, thereby reducing or substantially eliminating the phenotypic aspect which depends on the expression of the particular tumor associated gene.

As previously noted, the polypeptide products of tumor associated genes can be the targets for host immune surveillance and provoke selection and expansion of one or more clones of cytotoxic T lymphocytes specific for the tumor associated gene product. Examples of this phenomenon include proteins and fragments thereof encoded by the MAGE family of genes, the tyrosinase gene, the Melan-A gene, the BAGE gene, the GAGE gene, the RAGE family of genes, the PRAME gene and the brain glycogen phosphorylase gene, as are detailed below. Thus, tumor associated expression of genes suggests that such genes can encode proteins which will be recognized by the immune system as foreign and thus provide a target for tumor rejection. Such genes encode "tumor rejection antigen precursors", or TRAPs, which may be used to generate therapeutics for enhancement of the immune system response to tumors expressing such genes and proteins.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6-10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, *Science* 257: 880, 1992; Fremont et al., *Science* 257: 919, 1992; Matsumura et al., *Science* 257: 927, 1992; Latron et al., *Science* 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *J. Exp. Med.* 176:1453-1457, 1992; van der Bruggen et al., *Science* 254: 1643,1991; De Plaen et al., *Immunogenetics* 40:360-369, 1994 for further information on this family of genes. Also, see U.S. patent application Ser. No. 807,043, filed Dec. 12, 1991, now U.S. Pat. No. 5,342,774.

In U.S. patent application Ser. No. 938,334, now U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed.

This second TRA is presented by HLA-Cw16 molecules, also known as HLA-C*1601. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. patent application Ser. No. 08/032,978, filed Mar. 18, 1993, and incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

In U.S. patent application Ser. No. 079,110, filed Jun. 17, 1993 and entitled "Isolated Nucleic Acid Molecules Coding For BAGE Tumor Rejection Antigen Precursors" and Ser. No. 196,630, filed Feb. 15, 1994, and entitled "Isolated Peptides Which form Complexes with MHC Molecule HLA-C-Clone 10 and Uses Thereof" the entire disclosures of which are incorporated herein by reference, an unrelated tumor rejection antigen precursor, the so-called "BAGE" precursor, is described. TRAs are derived from the TRAP and also are described. They form complexes with MHC molecule HLA-C-Clone 10.

In U.S. patent application Ser. No. 096,039, filed Jul. 22, 1993 and entitled "Isolated Nucleic Acid Molecules Coding for GAGE Tumor Rejection Antigen Precursors" and Ser. No. 250,162, filed May 27, 1994 and entitled "Method for Diagnosing a Disorder by Determining Expression of GAGE Tumor Rejection Antigen Precursors", the entire disclosures of which are incorporated herein by reference, another unrelated tumor rejection antigen precursor, the so-called "GAGE" precursor, is described. The GAGE precursor is not related to the BAGE or the MAGE family.

In U.S. patent application Ser. No. 08/408,015, filed Mar. 21, 1995, and entitled "RAGE Tumor Rejection Antigen Precursors", incorporated herein by reference in its entirety, another TRAP is taught which is not derived from any of the foregoing genes. The TRAP is referred to as RAGE. In U.S. patent application Ser. No. 08/530,015, filed Sep. 20, 1995, and entitled "Isolated RAGE-1 Derived Peptides Which Complex with HLA-B7 Molecules and Uses Thereof", also incorporated by reference, the TRA derived form one member of the RAGE family of genes is taught to be presented by HLA-B7 molecules. This disclosure shows that additional TRAPs and TRAs can be derived from different sources.

In U.S. patent application Ser. No. 08/253,503, filed Jun. 3, 1994, and entitled "Isolated Nucleic Acid Molecule Which Codes for a Tumor Rejection Antigen Precursor Which is Processed to an Antigen Presented by HLA-B44", incorporated herein by reference in its entirety, another TRAP is taught which is not derived from any of the foregoing genes. The gene encoding the TRAP is referred to as MUM-1. A tumor rejection antigen, LB-33B, is described in the application.

In U.S. patent application Ser. No. 08/373,636, filed Jan. 17, 1995, and entitled "Isolated Nucleic Acid Molecule Which Codes for a Tumor Rejection Antigen Precursor Which is Processed to Antigens Presented by HLA Molecules and Uses Thereof", incorporated herein by reference in its entirety, other TRAPs are taught which are derived from LB33 and presented by HLA-B13, HLA-Cw6, HLA-A28 and HLA-A24.

In PCT publication WO96/10577, published Apr. 11, 1996, and entitled "Isolated Nucleic Acid Molecule Coding for a Tumor Rejection Antigen Precursor DAGE and Uses Thereof", incorporated herein by reference in its entirety, another TRAP is taught which is not derived from any of the foregoing genes. The TRAP was referred to as DAGE, but is now referred to as PRAME. A tumor rejection antigen is described in the application which is presented by HLA-A24.

In U.S. patent application Ser. No. 08/487,135, filed Jun. 7, 1995, and entitled "Isolated Nucleic Acid Molecule, Peptides Which Form Complexes with MHC Molecule HLA-A2 and Uses Thereof", incorporated herein by reference in its entirety, another TRAP is taught which is not derived from any of the foregoing genes. The TRAP is referred to as NAG. Various TRAs derived from NAG and presented by HLA-A2 are taught in this application.

In U.S. patent application Ser. No. 08/403,388, filed Mar. 14, 1995, and entitled "Isolated Nucleic Acid Molecules Which Are Members of the MAGE-Xp Family and Uses Thereof", incorporated herein by reference in its entirety, three TRAPs are taught which are not derived from any of the foregoing genes. These TRAPs are referred to as MAGE-Xp2, MAGE-Xp3 and MAGE-Xp4.

The work which is presented by the papers, patents and patent applications described above deal, for the most part, with the MAGE family of genes, the BAGE gene, the GAGE gene and the RAGE family of genes. It now has been discovered that additional genes similarly are expressed in a tumor associated pattern.

The invention is elaborated upon further in the disclosure which follows.

SUMMARY OF THE INVENTION

The genes which are believed to encode tumor rejection antigen precursors were referred to originally as LL-1 tumor associated genes (LL-1.1 and LL-1.2). One of the two genes, originally termed LL-1.2, is now known as NY-ESO-1 as described in U.S. patent application Ser. No. 08/725,182. The other LL-1 gene, LL-1.1, is now known as LAGE-1 and does not show homology to the MAGE family of genes, to the BAGE gene, the GAGE gene, the RAGE family of genes, the LB33/MUM-1 gene, the PRAME gene, the NAG gene or the MAGE-Xp family of genes. Thus the invention relates to the LAGE-1 gene expressed specifically in certain tumor cells, tumor rejection antigen precursors encoded by the LAGE-1 gene, as well as related molecules and applications of these various entities.

The invention provides isolated nucleic acid molecules, unique fragments of those molecules, expression vectors containing the foregoing, and host cells transfected with those molecules. The invention also provides isolated polypeptides and agents which bind such polypeptides, including antibodies. Kits for detecting the presence of a LAGE-1 tumor associated polypeptide precursor additionally are provided. The foregoing can be used in the diagnosis or treatment of conditions characterized by the expression of a LAGE-1 tumor-specific polypeptide or precursor thereof.

According to one aspect of the invention, an isolated nucleic acid molecule is provided. The molecule hybridizes under stringent conditions to a molecule having a nucleotide sequence selected from the group consisting of the nucleotide sequence of SEQ ID NO:4 and the nucleotide sequence of SEQ ID NO:6. The isolated nucleic acid molecule is a LAGE-1 tumor associated polypeptide precursor and codes for a LAGE-1 tumor associated polypeptide, including allelic variants of LAGE-1 tumor associated polypeptides. The invention further embraces nucleic acid molecules that differ from the foregoing isolated nucleic acid molecules in codon sequence to the degeneracy of the genetic code. The invention also embraces complements of the foregoing nucleic acids.

In preferred embodiments, the isolated nucleic acid molecule comprises a molecule selected from the group consisting of the nucleic acid sequence of SEQ ID NO:4 and the nucleic acid sequence of SEQ ID NO:6. More preferably, the isolated nucleic acid molecule comprises a molecule selected from the group consisting of the coding region of the nucleic acid sequence of SEQ ID. NO:4 and the coding region of the nucleic acid sequence of SEQ ID NO:6.

According to another aspect of the invention, an isolated nucleic acid molecule is provided which comprises a molecule selected from the group consisting of a unique fragment of nucleotides 1-993 of SEQ ID NO:4 between 12 and 992 nucleotides in length, a unique fragment of nucleotides 1-746 of SEQ ID NO:6 between 12 and 745 nucleotides in length, and complements thereof. The unique fragments exclude nucleic acid molecules which consist only of fragments of SEQ ID NO:8 and fragments of SEQ ID NO:8 having 5 or fewer contiguous nucleotides of SEQ ID NO:4 OR SEQ ID NO:6. In preferred embodiments, the unique fragment is at least 14, 15, 16, 17, 18, 20 or 22 contiguous nucleotides of nucleotides 1-993 of SEQ ID NO:4, nucleotides 1-746 SEQ ID NO:6, or complements thereof. In another embodiment, the isolated nucleic acid molecule consists of between 12 and 32 contiguous nucleotides of nucleotides 1-993 of SEQ ID NO:4, nucleotides 1-746 of SEQ ID NO:6, or complements of such nucleic acid molecules.

According to another aspect of the invention, the invention involves expression vectors, and host cells transformed or transfected with such expression vectors, comprising the nucleic acid molecules described above. The expression vectors and/or host cells preferably include a nucleic acid molecule which codes for a HLA molecule. Of course, an HLA-encoding nucleic acid molecule can also be contained in a separate expression vector.

According to another aspect of the invention, an isolated polypeptide encoded by a nucleic acid molecule which hybridizes under stringent conditions to a molecule selected from the group consisting of the nucleic acid sequence of SEQ ID NO:4 and the nucleic acid sequence of SEQ ID NO:6, nucleic acid molecules which vary from the foregoing according to the degeneracy of the genetic code, complements and allelic variants of any of the foregoing nucleic acid molecules. Preferred polypeptides are those which include the amino acid sequence of SEQ ID NO:5, the amino acid sequence of SEQ ID NO:7, the amino acid sequence of SEQ ID NO:5 or SEQ ID NO:7 having a glutamine to arginine substitution at residue 6, the amino acid sequence of SEQ ID NO:5 or SEQ ID NO:7 having a glutamine to glutamic acid substitution at residue 89, and the amino acid sequence of SEQ ID NO:5 having an arginine to tryptophan substitution at residue 138.

In another aspect of the invention, isolated LAGE-1 polypeptides which include amino acids 89-93 of SEQ ID NO:5 or 7 are provided. Preferred embodiments of such polypeptides include isolated LAGE-1 polypeptides which include amino acids 71-93, 71-98, 89-98, 89-111, or 71-111 of SEQ ID NO:5 or 7. Nucleic acids which encode such polypeptides also are provided.

According to another aspect of the invention, isolated LAGE-1b polypeptides which include amino acids 142-148 of SEQ ID NO:5, amino acids 187-205 of SEQ ID NO:5, or amino acids 164-179 of SEQ ID NO:5 are provided. Preferably such isolated polypeptides include amino acids 134-210 of SEQ ID NO:5. Isolated nucleic acids which encode such polypeptides also are provided.

According to yet another aspect of the invention, an isolated polypeptide is provided which comprises a molecule selected from the group consisting of a unique fragment of SEQ ID NO:5 between 9 and 209 amino acids in length and a unique fragment of SEQ ID NO:7 between 9 and 179 amino acids in length. The unique fragment is not a polypeptide consisting of fragments of SEQ ID NO:9. Preferably, the unique fragment of the isolated polypeptide binds to a polypeptide-binding agent. In preferred embodiments, the polypeptide-binding agent is an antibody or a cytotoxic T lymphocyte.

The invention also provides isolated polypeptides which selectively bind a LAGE-1 protein or fragments thereof. Isolated binding polypeptides include antibodies and fragments of antibodies (e.g., Fab, F(ab)$_2$, Fd and antibody fragments which include a CDR III region which binds selectively to the LAGE-1 proteins of the invention). The isolated binding polypeptides include monoclonal antibodies.

The invention in another aspect involves a kit for detecting the presence of the expression of a LAGE-1 tumor associated polypeptide precursor. Such kits employ two or more of the above-described molecules isolated in separate containers and packaged in a single package. In one such kit, a pair of isolated nucleic acid molecules is provided, each of the pair consisting essentially of a molecule selected from the group consisting of a 12-32 nucleotide contiguous segment of SEQ ID NO:4 and complements thereof, and a 12-32 nucleotide contiguous segment of SEQ ID NO:6 and complements thereof, wherein the contiguous segments are nonoverlapping. Preferably, the pair of isolated nucleic acid molecules is constructed and arranged to selectively amplify an isolated nucleic acid molecule which hybridizes under stringent conditions to a molecule selected from the group consisting of the nucleic acid sequence of SEQ ID NO:4, the nucleic acid sequence of SEQ ID NO:6, nucleic acid molecules which differ from the above in codon sequence due to the degeneracy of the genetic code, complements and allelic variants thereof. In certain embodiments, the pair of isolated nucleic acid molecules is PCR primers. Preferably one of the primers is a contiguous segment of SEQ ID NO:4 and another of the primers is a complement of another contiguous segment of SEQ ID NO:4. In other preferred embodiments, one of the primers is a contiguous segment of SEQ ID NO:6 and another of the primers is the complement of another contiguous segment of SEQ ID NO:6.

According to still another aspect of the invention, a method for diagnosing a disorder characterized by the expression of a LAGE-1 nucleic acid molecule or an expression product thereof is provided. The method involves contacting a biological sample isolated from a subject with an agent that selectively binds a LAGE-1 nucleic acid molecule or an expression product thereof. In certain embodiments, the nucleic acid molecule hybridizes under stringent conditions to a molecule selected from the group consisting of the nucleic acid sequence of SEQ ID NO:4 and the nucleic acid sequence of SEQ ID NO:6, and which codes for a tumor associated polypeptide. In other embodiments, the agent is a binding agent which selectively binds to a LAGE-1 tumor associated polypeptide, such as an antibody, cytotoxic T lymphocyte, polypeptide, and the like. The method further involves determining the interaction between the agent and the nucleic acid molecule or expression product thereof as a determination of the disorder. In preferred embodiments, the agent is a DNA molecule comprising SEQ ID NO:4 or SEQ ID NO:6, or a unique fragment thereof. In certain embodiments, the interaction between the agent and the nucleic acid molecule is determined by amplifying at least a portion of the nucleic acid molecule.

According to another aspect of the invention, a method for treating a subject with a disorder characterized by expression of an LAGE-1 tumor associated polypeptide is provided. The method involves administering to the subject an amount of an agent, which agent enriches selectively in the subject the presence of complexes of a HLA molecule and a tumor rejection antigen which is derived from a LAGE-1 tumor associated polypeptide coded for by one of the foregoing nucleic acid molecules. The amount of the agent administered is sufficient to ameliorate the disorder. Preferably the agent is a LAGE-1 polypeptide, or an immunogenic fragment thereof.

According to yet another aspect of the invention, a method for treating a subject with a disorder characterized by expression of a LAGE-1 nucleic acid molecule or an expression product thereof is provided. The method includes administering to the subject an amount of autologous cytolytic T cells sufficient to ameliorate the disorder, wherein the cytolytic T cells are specific for complexes of an HLA molecule and a LAGE-1 tumor associated polypeptide or an immunogenic fragment thereof.

In another aspect, the invention provides methods for treating a subject with a disorder characterized by expression of a LAGE-1 nucleic acid molecule or an expression product thereof. The methods include administering to the subject an amount of a LAGE-1 tumor associated polypeptide or an immunogenic fragment thereof sufficient to ameliorate the disorder.

According to another aspect of the invention, methods for enriching selectively a population of T cells with cytolytic T cells specific for a LAGE-1 tumor associated polypeptide are provided. The methods include contacting an isolated population of T cells with an agent presenting a complex of a LAGE-1 tumor associated polypeptide or an immunogenic fragment thereof and a HLA presenting molecule in an amount sufficient to selectively enrich the isolated population of T cells with the cytolytic T cells. Preferably the agent is a cell which expresses a LAGE-1 tumor associated polypeptide and a HLA molecule. In certain preferred embodiments, the LAGE-1 tumor associated polypeptide is encoded by a nucleic acid molecule having the nucleotide sequence of SEQ ID NO:4 or SEQ ID NO:6.

According to other aspects of the invention, vaccine compositions which include a nucleic acid encoding at least one LAGE-1 epitope, a LAGE-1 polypeptide and/or a cell which expresses LAGE-1 nucleic acid or polypeptide, or immunogenic fragments thereof, are provided. The vaccine compositions are useful for increasing an immune response in a subject.

Use of the foregoing compositions in the preparation of medicaments is also provided. In particular, use of the composition in the preparation of a medicament for treating cancer is provided.

These and other objects of the invention will be described in further detail in connection with the detailed description of the invention.

BRIEF DESCRIPTION OF THE SEQUENCES

Figure 1:
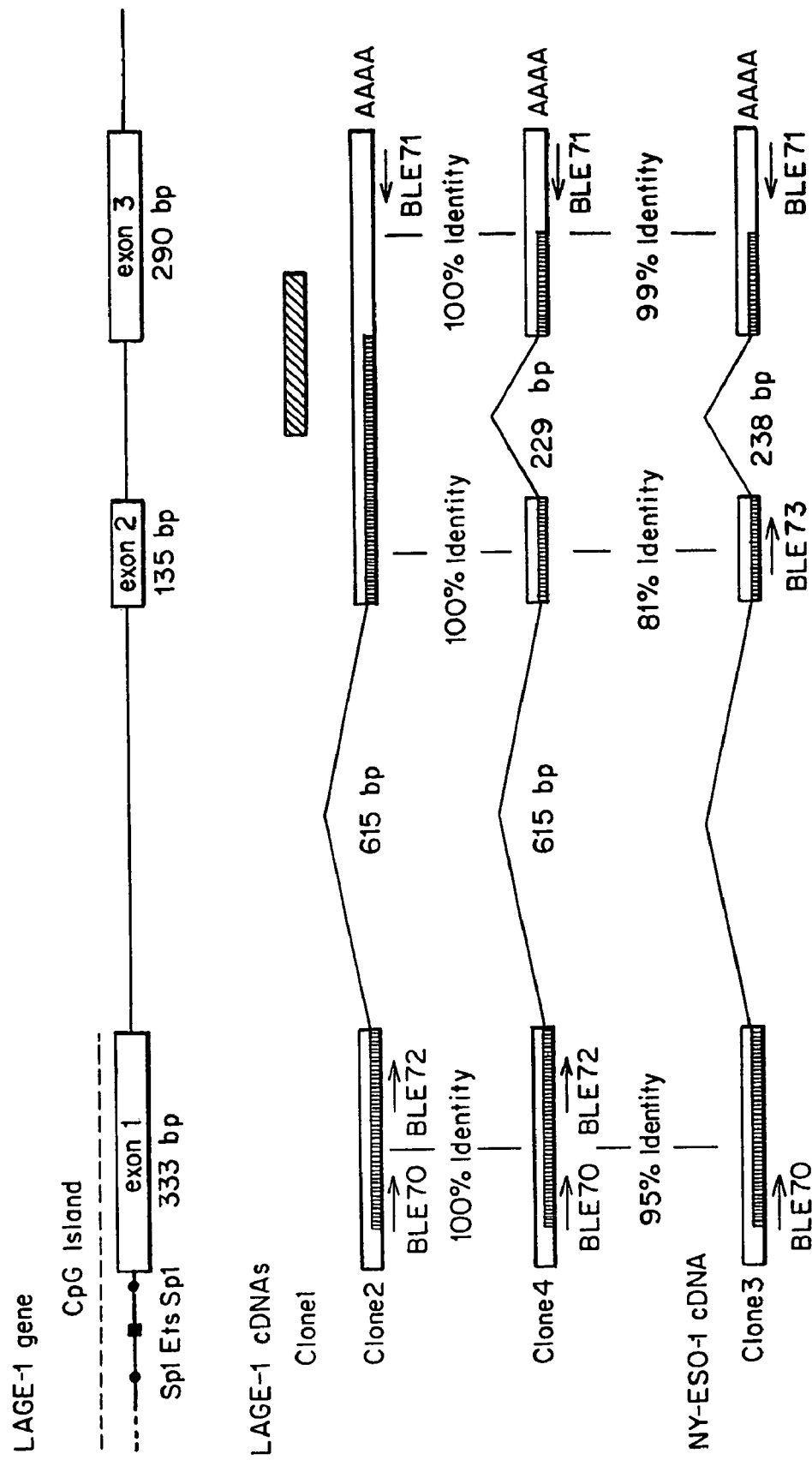
FIG. 1 depicts the nucleotide sequences of LL-1 clones 2, 3 and 4 (now known as LAGE-1 clone 2 [LAGE-1b], NY-ESO-1 and LAGE-1 clone 4 [LAGE-1a], respectively).

SEQ ID NO:1 is the nucleotide sequence of LAGE-1 clone 1.
SEQ ID NO:2 is the nucleotide sequence of primer SL25.
SEQ ID NO:3 is the nucleotide sequence of primer BLE56.
SEQ ID NO:4 is the nucleotide sequence of LAGE-1 clone 2, also known as LAGE-1b.
SEQ ID NO:5 is the amino acid sequence of the translation product of LAGE-1 clone 2.
SEQ ID NO:6 is the nucleotide sequence of LAGE-1 clone 4, also known as LAGE-1a.
SEQ ID NO:7 is the amino acid sequence of the translation product of LAGE-1 clone 4.
SEQ ID NO:8 is the nucleotide sequence of NY-ESO-1, formerly known as LL-1.2 clone 3.
SEQ ID NO:9 is the amino acid sequence of the translation product of NY-ESO-1, formerly known as LL-1.2 clone 3.
SEQ ID NO:10 is the nucleotide sequence of primer BLE70.
SEQ ID NO:11 is the nucleotide sequence of primer BLE71.
SEQ ID NO:12 is the nucleotide sequence of primer BLE72.
SEQ ID NO:13 is the nucleotide sequence of primer BLE73.
SEQ ID NO:14 is the nucleotide sequence of primer BLE74.

DETAILED DESCRIPTION OF THE INVENTION

The examples which follow show the isolation of nucleic acid molecules which code for polypeptides and are expressed preferentially in tumor samples and tumor-derived cell lines. These isolated nucleic acid molecules, however, are not homologous with any of the previously disclosed coding sequences described in the references set forth supra. Hence, one aspect of the invention is an isolated nucleic acid molecule which includes all or a unique portion of the nucleotide sequence set forth in SEQ ID NO:4 or SEQ ID NO:6. These sequences are not MAGE, BAGE, GAGE, RAGE, LB33/MUM-1, PRAME, NAG, MAGE-Xp or NY-ESO-1 sequences, as will be seen by comparing them to the sequence of any of the genes described in the references.

The invention thus involves LAGE-1 nucleic acids, polypeptides encoded by those nucleic acids, functional modifications and variants of the foregoing, useful fragments of the foregoing, as well as therapeutics and diagnostics related thereto.

Also a part of the invention are those nucleic acid sequences which also code for a LAGE-1 tumor associated polypeptide and which hybridize to a nucleic acid molecule consisting of the nucleotide sequence set forth in SEQ ID NO:4 (LAGE-1b) or SEQ ID NO:6 (LAGE-1a), under stringent conditions, but which are not nucleic acid molecules consisting of the nucleotide sequence set forth in SEQ ID NO:8 (NY-ESO-1). LAGE-1 nucleic acids are characterized by at least 90% identity with exon 2 of LAGE-1. Preferably the nucleic acid identity with exon 2 of LAGE-1 is at least 95% and most preferably is at least 99%. Complements of the foregoing are also embraced by the invention.

Other criteria for establishing that a nucleic acid is part of the LAGE-1 family are shown in FIG. 1. For example, in addition to the nucleotide sequence of the coding region of the LAGE-1 gene and expression products thereof, the length and composition of introns present in the LAGE-1 gene can be used to establish the relation of a nucleic acid to LAGE-1. Sequences upstream and downstream of the coding region also are useful for distinguishing LAGE-1 nucleic acids from non-LAGE-1 nucleic acids. The iso-electric point of the encoded proteins or fragments of the encoded proteins also can serve as distinguishing characteristics of nucleic acids related to LAGE-1.

Such nucleic acids are termed tumor associated polypeptide precursors, and may be DNA, RNA, or composed of mixed deoxyribonucleotides and ribonucleotides. The tumor associated polypeptide precursors can also incorporate synthetic non-natural nucleotides. A tumor associated nucleic acid or polypeptide is a nucleic acid or polypeptide expressed preferentially in tumor cells. Various methods for determining the expression of a nucleic acid and/or a polypeptide in normal and tumor cells are known to those of skill in the art and are described further below. As used herein, tumor associated polypeptides include proteins, protein fragments, and peptides. In particular, tumor associated polypeptides include TRAPs and TRAs.

The term "stringent conditions" as used herein refers to parameters with which the art is familiar. More specifically, stringent conditions, as used herein, refers to hybridization at 65° C. in hybridization buffer (3.5×SSC, 0.02% Ficoll, 0.02% polyvinyl pyrolidone, 0.02% Bovine Serum Albumin, 25 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetracetic acid. After hybridization, the membrane upon which the nucleic acid is transferred is washed at 2×SSC at room temperature and then at 0.1×SSC/0.1×SDS at 65° C. SSC is 0.15M sodium chloride/0.15M sodium citrate, pH 7; SDS is sodium dodecyl sulphate; and EDTA is ethylenediamine tetraacetic acid.

There are other conditions, reagents, and so forth which can be used, which result in the same degree of stringency (see, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York). The skilled artisan will be familiar with such conditions, and thus they are not given here. It will be understood, however, that the skilled artisan will be able to manipulate the conditions in a manner to permit the clear identification of homologs and alleles of LAGE-1 nucleic acid molecules of the invention. The skilled artisan also is familiar with the methodology for screening cells, preferably cancer cells, and libraries for expression of such molecules which then are routinely isolated, followed by isolation of the pertinent nucleic acid and sequencing.

The nucleic acids disclosed herein are useful for determining the expression of LAGE-1 according to standard hybridization procedures. The nucleic acids also can be used to express LAGE-1 polypeptides in vitro or in vivo. The nucleic acids also can be used to prepare fragments of LAGE-1 polypeptides useful for e.g., preparation of antibodies. Many other uses will be apparent to the skilled artisan.

In screening for LAGE-1 family members, a Southern blot may be performed using the foregoing conditions, together with a radioactive probe. Preferably hybridizations are performed using probes comprising LAGE-1 exon2 and/or intron 2, or portions thereof. After washing the membrane to which the nucleic acid is finally transferred, the membrane can be placed against x-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:4 or SEQ ID NO:6, or complements of SEQ ID NO:4 or SEQ ID NO:6. A unique fragment is one that is a 'signature' for the larger nucleic acid. It, for example, is long enough to assure that its precise sequence is not found in molecules outside of the LAGE-1 family as defined by claim 1. In particular, a unique fragment of LAGE-1 is one which would not hybridize under stringent conditions to a nucleic acid molecule having the nucleotide sequence of SEQ ID NO:8. Unique fragments can be used as probes in Southern blot assays to identify family members or can be used in amplification assays such as those employing PCR. As known to those skilled in the art, large probes such as 200 nucleotides or more (e.g., 200, 250, 300, 400, 500 nucleotides) are preferred for certain uses such as Southern blots, while smaller fragments will be preferred for uses such as PCR. Unique fragments also can be used to produce fusion proteins for generating antibodies or for generating immunoassay components. Unique fragments further can be used as antisense molecules to inhibit the expression of the LAGE-1 proteins of the invention, particularly for therapeutic purposes as described in greater detail below.

As will be recognized by those skilled in the art, the size of the unique fragment will depend upon its conservancy in the genetic code. Thus, some regions of SEQ ID NO:4 or SEQ ID NO:6, and their complements, will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 nucleotides long). Virtually any segment of SEQ ID NO:4 or SEQ ID NO:6, or their complements, that is 18 or more nucleotides in length will be unique. Unique fragments of LAGE-1, however, exclude fragments completely composed of the nucleotide sequence of SEQ ID NO:8 (encoding the NY-ESO-1 polypeptide) which overlaps SEQ ID NO:4 or SEQ ID NO:6. A fragment which is completely composed of the sequence of SEQ ID NO:8 is one which does not include any of the nucleotides unique to LAGE-1. In certain embodiments, unique fragments of LAGE-1 include at least 5 contiguous nucleotides which are not present in SEQ ID NO:8 (e.g. which are present in SEQ ID NO:4 or SEQ ID NO:6); preferred unique fragments are those which have 6, 7, 8, 9, 10, 12, 14, 16, 18, 20, or more nucleotides which are not present in SEQ ID NO:8. Thus a molecule consisting of a fragment of SEQ ID NO:8 with 4 nucleotides of SEQ ID NO:4 or SEQ ID NO:6 added on the 5' or 3' end is not a unique fragment. Those skilled in the art are well versed in methods for selecting such sequences, typically on the basis of the ability of the unique fragment to selectively distinguish the sequence of interest from non-family members. A comparison of the sequence of the LAGE-1 fragment to the NY-ESO-1 nucleic acid sequence and to other sequences deposited in known data bases typically is all that is necessary, although in vitro confirmatory hybridization and sequencing analysis may be performed.

For any pair of PCR primers constructed and arranged to selectively amplify, for example, a LAGE-1 nucleic acid, a LAGE-1 specific primer may be used. Such a primer is a contiguous stretch of LAGE-1 which hybridizes selectively to LAGE-1 and not other nucleic acids. Such a specific primer would fully hybridize to a contiguous stretch of nucleotides only in LAGE-1, but would hybridize at most only in part to genes that do not share the nucleotides to which the LAGE-1 specific primer binds. For efficient PCR priming and LAGE-1 identification, the LAGE-1 specific primer should be constructed and arranged so it does not hybridize efficiently at its 3' end to genes other than LAGE-1. The kinetics of hybridization then will strongly favor hybridization at the 5' end. In this instance, 3' initiated PCR extension will occur only when both the 5' and 3' ends hybridize to the nucleic acid. Primers for selective amplification of LAGE-1 clone 2 and/or LAGE-1 clone 4 can be selected from portions of LAGE-1 which share lesser homology with NY-ESO-1 (see FIG. 1; compare SEQ ID NO:4, SEQ ID NO:6 and SEQ ID NO:8). In such cases, the LAGE-1 specific primers can be designed to prime DNA synthesis on either strand of the LAGE-1 gene, described herein as the antisense or the sense strands. Preferably the area of non-identity is at least one to four nucleotides in length and forms the 3' end of the LAGE-1 specific primer. Such a primer would be perfectly complementary and contiguous with its complement in LAGE-1. The 3' end of the primer would hybridize to its complement in the antisense strand and initiate extension. In genes other than LAGE-1, the lack of nucleotide sequence identity would substantially eliminate hybridization of the 3' end of the LAGF, 1 specific primer to the antisense strand 5' of the insert. The mismatch generated at the 3' end of the primer when hybridized to genes other than LAGE-1 would preclude efficient amplification of those genes. Exemplary primers include BLE72 (SEQ ID NO:12) which spans nucleotides 265-283 of SEQ ID NO:6. Other primers which contain nucleotide sequences not found in NY-ESO-1 can be prepared by one of skill in the art by comparison of the sequences of SEQ ID NO:4 or SEQ ID NO:6 with SEQ ID NO:8. Portions of SEQ ID NO:6 identical to SEQ ID NO:4 would serve equally well as LAGE-1 specific primers. Other exemplary primers can differ from the above by addition or deletion of 1, 2, 3, 4, 5, or more nucleotides from the 5' end of the primer.

Similarly, one of ordinary skill in the art can select primers from the nucleotide sequence of SEQ ID NO:8 for selective amplification of NY-ESO-1 mRNA sequences. For example, exemplary primers specific for NY-ESO-1 include BLE73 (SEQ ID NO:13), and BLE74 (SEQ ID NO:14) which is a sense primer located in SEQ ID NO:8 at nucleotides 262-281 (homologous to the position of BLE72 in SEQ ID NO:6, e.g., nucleotides 264-283). As demonstrated in the Examples below, primer pairs specific to LAGE-1 or NY-ESO-1 can be used to distinguish the expression of the genes in cells and tissues. Other exemplary primers can differ from the above by addition or deletion of 1, 2, 3, 4, 5, or more nucleotides from the 5' end of the primers above. One of ordinary skill in the art can determine with no more than routine experimentation the preferred primers for selective amplification of particular LAGE-1 clones.

In certain cases, the primers chosen to distinguish the LAGE-1 clones provide amplified products which are readily distinguishable by molecular size. For example, LAGE-1 primers can be chosen which initiate extension on opposite sides of the splice site by hybridizing to sequences which are identical or nearly so and which hybridize 5' of the 5' splice site and 3' of the 3' splice site. Because LAGE-1 clone 2 mRNA contains a portion of the gene which is spliced out in formation of LAGE-1 clone 4 mRNA (see FIG. 1; i.e., nucleotides 469-697 of SEQ ID NO:4), amplification products derived from LAGE-1 clone 2 using such primers will be longer than amplification products derived from LAGE-1 clone 4 (by about 229 base pairs). This difference may be distinguished readily using standard methods in the art including agarose and acrylamide gel electrophoresis.

Additional methods which can distinguish nucleotide sequences of substantial homology, such as ligase chain reaction ("LCR") and other methods, will be apparent to skilled artisans.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The invention also provides isolated polypeptides which include unique fragments of SEQ ID NO:5 or SEQ ID NO:7. Such polypeptides are useful, for example, alone or as fusion proteins to generate antibodies, as a components of an immunoassay, or for determining the LAGE-1 protein binding specificity of HLA molecules and/or CTL clones. The term "isolated", as used herein in reference to a polypeptide, means a polypeptide encoded by an isolated nucleic acid sequence, as well as polypeptides synthesized by, for example, chemical synthetic methods, and polypeptides separated from biological materials, and then purified using conventional protein analytical or preparatory procedures. Thus LAGE-1 proteins include polypeptides having amino acids 89-93 of SEQ ID NO:5 or 7. Preferred embodiments of such polypeptides include LAGE-1 polypeptides which include amino acids 71-93, 71-98, 89-98, 89-111, or 71-111 of SEQ ID NO:5 or 7. The foregoing amino acid sequences are not found in the NY-ESO-1 protein. Nucleic acids which encode the foregoing polypeptides also are embraced by the invention. LAGE-1b polypeptides which include amino acids encoded by the alternatively spliced intron 2 of LAGE-1 also are provided. These polypeptides in certain embodiments contain amino acids 142-148 of SEQ ID NO:5, amino acids 187-205 of SEQ ID NO:5, or amino acids 164-179 of SEQ ID NO:5. Preferably such polypeptides include amino acids 134-210 of SEQ ID NO:5. These amino acid sequences are not found in the NY-ESO-1 or LAGE-1a proteins. Nucleic acids which encode such LAGE-1b polypeptides also are embraced by the invention. Preferably, a LAGE-1 protein is at least 90%, more preferably 95%, and most preferably 99% identical to the amino acid sequence set forth in either SEQ ID NO:5 or SEQ ID NO:7.

A unique fragment of an LAGE-1 protein, in general, has the features and characteristics of unique fragments as discussed above in connection with nucleic acids. Thus a protein fragment which consists only of a portion of SEQ ID NO:9 is not a unique fragment of LAGE-1. As will be recognized by those skilled in the art, the size of the unique fragment will depend upon factors such as whether the fragment constitutes a portion of a conserved protein domain. Thus, some regions of SEQ ID NO:5 and SEQ ID NO:7, will require longer segments to be unique while others will require only short segments, typically between 5 and 12 amino acids (e.g. 5, 6, 7, 8, 9, 10, 11 and 12 amino acids long). Virtually any segment of SEQ ID NO:5 or SEQ ID NO:7 which excludes SEQ ID NO:9, that is 10 or more amino acids in length will be unique. Preferably, unique fragments of LAGE-1 include at least 2, more preferably 3 and most preferably 5 contiguous amino acids which are not present in SEQ ID NO:9 (e.g. which are present in SEQ ID NO:5 or SEQ ID NO:7).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding of nucleic acids, and enzymatic activity. A tumor rejection antigen is an example of a unique fragment of a tumor associated polypeptide which retains the functional capability of HLA binding and interaction with cytotoxic T lymphocytes. Tumor rejection antigens presented by HLA class I molecules typically are 9 amino acids in length, although peptides of 8, 9 and 10 and more amino acids also retain the capability to interact with HLA and cytotoxic T lymphocyte to an extent effective to provoke a cytotoxic T lymphocyte response (see, e.g., Van den Eynde & Brichard, *Curr. Opin. Immunol.* 7:674-681, 1995; Coulie et al., *Stem Cells* 13:393-403, 1995).

Those skilled in the art are well versed in methods for selecting unique amino acid sequences, typically on the basis of the ability of the unique fragment to selectively distinguish the sequence of interest from non-LAGE-1 family polypeptides, particularly NY-ESO-1. A comparison of the sequence of the fragment to those on known data bases typically is all that is necessary. Certain functional aspects of unique fragments of the LAGE-1 polypeptides can be determined by employing well-known computer algorithms to compare LAGE-1 fragments to fragments of other polypeptides. For example, an HLA-peptide binding algorithm (available on the National Institutes of Health website [bimas.dcrt.nih.gov]; Parker et al., *J. Immunol.* 152:163, 1994) can be used to distinguish the HLA binding properties of LAGE-1 peptides from those of NY-ESO-1 peptides. For example, the HLA-B7 binding score (half time of dissociation) of a LAGE-1 peptide containing amino acids 114-123 of SEQ ID NO:7 is predicted to be 30-fold greater than a NY-ESO-1 peptide having the corresponding amino acids (114-123) of SEQ ID NO:9.

The skilled artisan will also realize that conservative amino acid substitutions may be made in LAGE-1 polypeptides to provide functionally active homologs of the foregoing polypeptides, i.e, the homologs retain the functional capabilities of the LAGE-1 polypeptides. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Functionally equivalent variants of LAGE-1 polypeptides, i.e., variants of LAGE-1 polypeptides which retain the function of the natural LAGE-1 polypeptides, can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the LAGE-1 polypeptides include conservative amino acid substitutions of SEQ ID NO:5 and SEQ ID NO:7. Conservative amino-acid substitutions in the amino acid sequence of LAGE-1 polypeptides to produce functionally equivalent variants of LAGE-1 polypeptides typically are made by alteration of the nucleic acid encoding LAGE-1 polypeptides (SEQ ID NO:4, SEQ ID NO:6). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a LAGE-1 polypeptide. Where amino acid substitutions are made to a small unique fragment of a LAGE-1 polypeptide, such as a 9 amino acid peptide, the substitutions can be made by directly synthesizing the peptide. The activity of functionally equivalent fragments of LAGE-1 polypeptides can be tested by cloning the gene encoding the altered LAGE-1 polypeptide into a bacterial or mammalian expression vector, introducing the vector into an appropriate host cell, expressing the altered LAGE-1 polypeptide, and testing for a functional capability of the LAGE-1 polypeptides as disclosed herein.

As mentioned above, the invention embraces antisense oligonucleotides that selectively bind to a nucleic acid molecule encoding an LAGE-1 protein, to decrease transcription and/or translation of LAGE-1 genes. This is desirable in virtually any medical condition wherein a reduction in LAGE-1 gene product expression is desirable, including to reduce any aspect of a tumor cell phenotype attributable to LAGE-1 gene expression. Antisense molecules, in this manner, can be used to slow down or arrest such aspects of a tumor cell phenotype.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:4 and/or SEQ ID NO:6, or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7

(Wagner et al., *Nature Biotechnology* 14:840-844, 1996) and, more preferably, at least 15 consecutive bases which are complementary to the target. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind. Finally, although, SEQ ID Nos:4 and 6 disclose cDNA sequences, one of ordinary skill in the art may easily derive the genomic DNA corresponding to the cDNAs of SEQ ID Nos:4 and 6. Thus, the present invention also provides for antisense oligonucleotides which are complementary to the genomic DNA corresponding to SEQ ID Nos:4 and 6. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., *Nature Biotechnology* 14:840-844, 1996). The present invention, thus, contemplates pharmaceutical preparations containing modified antisense molecules that are complementary to and hybridizable with, under physiological conditions, nucleic acids encoding LAGE-1 proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

It will also be seen from the examples that the invention embraces the use of the LAGE-1 sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, including mast cells, fibroblasts, oocytes and lymphocytes, and they may be primary cells or cell lines. Specific examples include dendritic cells, U293 cells, peripheral blood leucocytes, bone marrow stem cells and embryonic stem cells. The expression vectors require that the pertinent sequence, i.e., those nucleic acids described supra, be operably linked to a promoter. As it is believed that a human HLA class I molecule presents a tumor rejection antigen derived from these genes, the expression vector may also include a nucleic acid sequence coding for the HLA molecule that presents any particular tumor rejection antigen derived from these genes and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for the tumor rejection antigen precursor and the HLA molecule which presents it are contained on separate expression vectors, the expression vectors can be cotransfected. The tumor rejection antigen precursor coding sequence may be used alone, when, e.g. the host cell already expresses a HLA molecule which presents a LAGE-1 TRA. Of course, there is no limit on the particular host cell which can be used. As the vectors which contain the two coding sequences may be used in any antigen-presenting cells if desired, and the gene for tumor rejection antigen precursor can be used in host cells which do not express a HLA molecule which presents a LAGE-1 TRA. Further, cell-free transcription systems may be used in lieu of cells.

The skilled artisan can determine which HLA molecule binds to tumor rejection antigens derived from LAGE-1 clone 2 and/or LAGE-1 clone 4 tumor rejection antigen precursors by, e.g., experiments utilizing antibodies to block specifically individual HLA class I molecules. For example, antibodies which bind selectively to HLA-A2 will prevent efficient presentation of TRAs specifically presented by HLA-A2. Thus, if TRAs derived from LAGE-1 are presented by HLA-A2, then the inclusion of anti-HLA-A2 antibodies in an in vitro assay will block the presentation of the LAGE-1 TRA. An assay for determining the nature of the HLA molecule is found in U.S. patent application Ser. No. 08/530,569. Briefly, in determining the HLA molecule type, inhibition experiments were carried out where the production of tumor necrosis factor (TNF) by cytotoxic T lymphocyte (CTL) clone 263/17 was tested in the presence of monoclonal antibodies directed against HLA molecules or against CD4/CD8 accessory molecules. Four monoclonal antibodies were found to inhibit the production of TNF by CTL 263/17: monoclonal antibody W6/32, which is directed against all HLA class I molecules (Parham et al., *J. Immunol.* 123:342, 1979), antibody B1.23.2 which recognizes HLA-B and C molecules (Rebai et al., *Tissue Antigens* 22:107, 1983), antibody ME-1 which specifically recognizes HLA-B7 (Ellis et al., *Hum. Immunol.* 5:49, 1982) and antibody B9.4.1 against CD8. No inhibition was found with antibodies directed against HLA Class II DR molecules (L243: Lampson et al., *J. Immunol.* 125:293, 1980), against HLA-A3 (GAPA 3: Berger et al., *Hybridoma* 1:87, 1982) or against CD4 (13B.8.82). The conclusion was that CTL 263/17 was of the CD8 type, and recognized an antigen presented by HLA-B7. Similar experiments using widely available anti-HLA antibodies can be performed to determine the nature of a HLA molecule.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See *Molecular Cloning: A Laboratory Manual*, J. Sambrook, et al., eds., Second Edition, Cold Spring Harbor Laboratory Press, Cold Spring Harbor, New York, 1989. Cells are genetically engineered by the introduction into the cells of heterologous DNA (RNA) encoding the LAGE-1 tumor associated polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, San Diego, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal ionjection in mice for immunization against P1A (*Int. J Cancer,* 67:303-310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also involves agents which bind to LAGE-1 polypeptides and in certain embodiments preferably to unique fragments of the LAGE-1 polypeptides. Such binding partners can be used in screening assays to detect the presence or absence of the LAGE-1 polypeptide and in purification protocols to isolate LAGE-1 polypeptides. Likewise, such binding partners can be used to selectively target drugs, toxins or other molecules to tumor cells which present LAGE-1 tumor associated polypeptides. In this manner, tumor cells which express LAGE-1 polypeptides can be treated with cytotoxic compounds.

The invention, therefore, involves antibodies or fragments of antibodies having the ability to selectively bind to LAGE-1 polypeptides, and preferably to unique fragments thereof. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to LAGE-1 polypeptides. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to a LAGE-1 polypeptide. This process can be is repeated through several cycles of reselection of phage that bind to the LAGE-1 polypeptide. Repeated rounds lead to enrichment of phage bearing particular sequences. DNA sequence analysis can be conducted to identify the sequences of the expressed polypeptides. The minimal linear portion of the sequence that binds to the LAGE-1 polypeptide can be determined. One can repeat the procedure using a biased library containing inserts containing part or all of the minimal linear portion plus one or more additional degenerate residues upstream or downstream thereof. Thus, the LAGE-1 polypeptides of the invention can be used to screen peptide libraries, including phage display libraries, to identify and select peptide binding partners of the LAGE-1 polypeptides of the invention. Such molecules can be used, as described, for screening assays, for diagnostic assays, for purification protocols or for targeting drugs, toxins and/or labeling agents (e.g. radioisotopes, fluorescent molecules, etc.) to cells which present LAGE-1 polypeptides on the cell surface. Such binding agent molecules can also be prepared to bind complexes of an LAGE-1 polypeptide and an HLA molecule by selecting the binding agent using such complexes. Drug molecules that would disable or destroy tumor cells which express such complexes or LAGE-1 polypeptides are known to those skilled in the art and are commercially available. For example, the immunotoxin art provides examples of toxins which are effective when delivered to a cell by an antibody or fragment thereof. Examples of toxins include ribosome-damaging toxins derived from plants or bacterial such as ricin, abrin, saporin, *Pseudomonas* endotoxin, diphtheria toxin, A chain toxins, blocked ricin, etc.

The invention as described herein has a number of uses, some of which are described herein. First, the invention permits the artisan to diagnose a disorder characterized by expression of the TRAP. These methods involve determining expression of the TRAP gene, and/or TRAs derived therefrom. In the former situation, such determinations can be carried out via any standard nucleic acid determination assay, including the polymerase chain reaction as exemplified in the examples below, or assaying with labeled hybridization probes.

The isolation of the TRAP gene also makes it possible to isolate the TRAP molecule itself, especially TRAP molecules containing the amino acid sequences coded for by SEQ ID NO:4 or SEQ ID NO:6. A variety of methodologies well-known to the skilled practitioner can be utilized to obtain isolated TRAP molecules. The protein may be purified from cells which naturally produce the protein. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce protein. Those skilled in the art also can readily follow known methods for isolating proteins in order to obtain isolated TRAPs. These include, but are not limited to, immunochromotography, HPLC, size-exclusion chromatography, ion-exchange chromatography and immune-affinity chromatography.

These isolated molecules when processed and presented as the TRA, or as complexes of TRA and HLA, such as HLA-A1, HLA-A2, or HLA-B7, may be combined with materials such as adjuvants to produce vaccines useful in treating disorders characterized by expression of the TRAP molecule. In addition to LAGE-1 peptides, nucleic acids which encode LAGE peptide epitopes can be used to prepare vaccines. Preparation of nucleic acids and/or peptides for use in vaccines is well known in the art. When "disorder" is used herein, it refers to any pathological condition where the tumor rejection antigen precursor is expressed. An example of such a disorder is cancer, melanoma in particular.

In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection.

Therapeutic approaches based upon the disclosure are premised on a response by a subject's immune system, leading to lysis of TRA presenting cells, such as HLA-B7 cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a COS cell of the type described supra. These transfectants present the desired complex of their surface and, when combined with a CTL of interest, stimulate its proliferation. COS cells, such as those used herein are widely available, as are other suitable host cells. Specific production of a CTL is well known to one of ordinary skill in the art. The clonally expanded autologous CTLs then are administered to the subject. Other CTLs specific to LAGE-1 clone 2 and/or LAGE-1 clone 4 may be isolated and administered by similar methods.

To detail a therapeutic methodology, referred to as adoptive transfer (Greenberg, *J. Immunol.* 136(5): 1917, 1986; Riddel et al., *Science* 257: 238, 1992; Lynch et al, *Eur. J. Immunol.* 21: 1403-1410, 1991; Kast et al., *Cell* 59: 603-614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a LAGE-1 sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a LAGE-1 derived TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex. Chen et al., *Proc. Natl. Acad. Sci. USA* 88: 110-114 (1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a LAGE-1 TRA may be operably linked to promoter and enhancer sequences which direct expression of the LAGE-1 TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding LAGE-1 TRAs. Nucleic acids encoding a LAGE-1 TRA also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous CTLs, which then proliferate.

A similar effect can be achieved by combining a TRAP or a stimulatory fragment thereof with an adjuvant to facilitate incorporation into HLA presenting cells in vivo. The TRAP is processed to yield the peptide partner of the HLA molecule while the TRA is presented without the need for further processing. Generally, subjects can receive an intradermal injection of an effective amount of LAGE-1 TRAP, and/or TRAs derived therefrom. Initial doses can be followed by booster doses, following immunization protocols standard in the art.

Yet another approach which can be utilized to provoke an immune response is to provide LAGE-1 TRAs in the form of a nucleic acid encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generated individual epitopes which are recognized by the immune system for generation of immune responses.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432-1434, 1995).

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Example 1

Isolation of a Sequence Specifically Expressed by Melanoma Cell Line LB373-MEL

Specific cDNA fragments of melanoma cell line LB373-MEL4.0 were enriched by subtraction of cDNA fragments found in LB243 normal skin cells, according to the representational difference analysis method (RDA) described for DNA by Hubank and Schatz (*Nucl. Acids Res.* 22: 5640-5648, 1994).

Briefly, cellular cDNAs obtained by reverse transcription of poly-A RNA of both LB373-MEL4.0 cells and LB243 normal skin cells primed with oligo-dT were digested by restriction enzyme DpnII. The DpnII fragments of cDNAs of each origin (LB373-MEL or LB243 normal skin cells) were ligated with the same set of adapters, divided in several groups and separately amplified by PCR. The PCR products originating from the same sample were pooled and digested again by DpnII. The DpnII fragments from the LB373-MEL cell line (the "tester" cDNA) were ligated with a new adapter set and hybridized with an excess of DpnII DNA fragments derived from the normal skin (the "driver" cDNA). The hybridization mixture was then submitted to PCR amplification using the new adaptor set. Only those DpnII fragments derived from the tester DNA but not present in the driver DNA were expected to be amplified exponentially because they carry primer-complementary sequences at both ends. These tester-specific amplification products were then cloned.

Thirty melanoma-cell specific cDNA clones obtained by this enrichment procedure were sequenced and compared with sequences compiled in databases. Some of the cDNA clones corresponded to known genes with ubiquitous expression, some of the cDNA clones corresponded to tumor associated genes (MAGE-3, MAGE-10, PRAME—formerly known as DAGE) and some of the cDNA clones were unknown. Among the six unknown clones, one melanoma-specific cDNA, LAGE-1 clone 1 (SEQ ID NO:1) which was formerly named LL-1 clone 1, appeared to have tumor associated expression as determined by RT-PCR. The LAGE-1 clone 1 was sequenced and determined to be 217 base pairs long.

To determine the pattern of expression of LAGE-1, RT-PCR of samples from various tumor and normal tissues was performed. Total RNA of normal tissue and tumor samples was converted to cDNA. An amount of DNA corresponding to 50 ng of total RNA was then amplified by thirty-two cycles (denature at 94° C. for 60 seconds, anneal at 58° C. for 60 to seconds, and extension at 72° C. for 90 seconds) followed by a final extension step of 10 minutes at 73° C., using primers SL25 (SEQ ID NO:2) and BLE56 (SEQ ID NO:3), with 0.5U DYNAZYME™ in a buffer, provided by the supplier (Finnzyme, Finland), containing 10 mM TRIS (pH8.8), 50 mM KCl and 1.5 mM $MgCl_2$. The total volume of the reaction mixture was 25 µl. Ten microliters were separated by electrophoresis on agarose gels. A fragment of the expected size was generated from cDNA of the parental LB373-MEL cell line and testis. No PCR product was obtained from normal skin cDNA starting materials, nor from a panel of cDNAs from eight other normal tissues. A faint signal was observed in one normal uterus sample.

Example 2

Isolation of Complete LAGE-1 cDNA Clones from Melanoma Cell Line LB373-MEL

A LB373-MEL cDNA library was prepared by reverse transcription of poly-A RNA with an oligo-dT/NotI primer using the Superscript II kit of BRL (Life Technologies, Gaithersburg, Md.). BstXI adapters were ligated to the ends of the cDNA, and the double stranded cDNA was digested with NotI. These fragments were then cloned into plasmid pCDNA I/Amp digested with BstXI and NotI.

To identify full-length LAGE-1 cDNA clones, we used the 137 bp PCR product amplified with primers SL25 (SEQ ID NO:2) and BLE56 (SEQ ID NO:3), as a probe to screen 75,000 clones of a cDNA library of LB373-MEL cells. The cDNA library was hybridized with the radiolabeled probe and washed according to standard protocols using 0.4×SSC at 63° C. The reduced stringency washing conditions were selected to maximize detection of related cDNA clones. DNA from 25 colonies hybridized to the LAGE-1 probe (0.03% of the total number of colonies), some of which DNAs were isolated and sequenced.

Two clones had sequence identity with the cDNA clone originally isolated from LB373-MEL cells (see Example 1, "clone 1" in FIG. 1). One of the clones contained a sequence that was identical to the 217 base pairs of LAGE-1 clone 1. This cDNA, referred to as LAGE-1 clone 2 (SEQ ID NO:4, FIG. 1) was determined to be about 993 nucleotides long excluding the poly A tail. Another hybridizing clone contained a sequence identical to the last 82 base pairs of LAGE-1 clone 1. This second cDNA, referred to as clone 3 (SEQ ID NO:8, FIG. 1), was determined to be about 744 nucleotides in length excluding the poly A tail. Clone 3 is now known to be NY-ESO-1 (see Chen et al., *Proc. Natl. Acad Sci. USA*. 94(5):1914-1918, 1997) The sequences of clone 2 and clone 3 were 94% identical. Most of the differences in nucleotide sequence between the two clones were located in the central region of the cDNAs. A third hybridizing clone, clone 4 (SEQ ID NO:6, FIG. 1), was determined to be about 746 nucleotides in length excluding the poly A tail. Analysis of the genomic fragment corresponding to LAGE-1 indicated that the region encompassing nucleotides 469-697 of clone 2 in FIG. 1 is an intron which was not spliced out during the formation of the LAGE-1 clone 2 mRNA.

In all clones, the longest open reading frame (ORF) is believed to begin at the same first ATG in a good transcription initiating context (gccATGc) according to Kozak (*J. Biol. Chem*. 266: 19867-19870, 1991). The size of the product of translation of completely spliced sequences of clone 4 (SEQ ID NO:6) and clone 3 (SEQ ID NO:8) derived from genes LAGE-1 and NY-ESO-1 respectively are believed to be in good agreement with the corresponding ORF (about 19-20 kD for 180 amino acids). The sequence of the putative protein encoded by NY-ESO-1 is referred to as SEQ ID NO:9. The translation product of partially spliced messenger RNAs (clone 2) from LAGE-1 has an apparent mass of about 25 kDa as determined by SDS-PAGE analysis of protein prepared by in vitro translation.

Example 3

Expression of LAGE-1 Genes in Normal Tissue and Tumor Samples

To determine the tissue specificity of expression of both LAGE-1 and NY-ESO-1 clones by PCR, we used two primers which correspond to sequences where LAGE-1 and NY-ESO-1 are identical. Primers BLE70 (SEQ ID NO:10) and BLE71 (SEQ ID NO:11), encompassing the main ORF, repeatedly provided two signals of nearly 600 base pairs and 850 base pairs which correspond to the fragment sizes of 614 and 842 base pairs expected for the spliced and unspliced LAGE-1 and NY-ESO-1 cDNAs.

A. Normal Tissues

RT-PCR with primers BLE70 and BLE71 was performed as described in Example 1, except that 20 cycles (denature at 95° C. for 30 seconds, anneal at 60° C. for 1 minute and extension at 70° C. for 3 minutes) were performed followed by 10 cycles with an extension time of 10 minutes at 70° C. and 15 minutes at 72° C. for the final extension. In addition, the buffer used was 50 mM Tris-HCl, pH9.2 (25° C.), 16 mM $(NH_4)_2SO_4$, 2.25 mM $MgCl_2$, 2% (v/v) DMSO and 0.1 % (v/v) TWEEN™ 20 (buffer 3 from Expand Long template of Boehringer). Analysis of amplification products was performed by agarose gel electrophoresis of 10 µl of the 25 µl total volume. Samples of various tissue origins were tested again with primers BLE71 and either BLE72 (SEQ ID NO:12, specific for LAGE-1) or BLE73 (SEQ ID NO:13, specific for NY-ESO-1), for 30 cycles with an annealing step at 62° C. for 1 minute and an extension step at 72° C. for 2 minutes using 0.5U Dynazyme according to manufacturer's instructions. The LAGE-1 PCR products were 399 and 628 bp, and the NY-ESO-1 product was 274 bp. Since the 628 bp product systematically appeared in shorter PCR product (spliced), only the latter is reported in Table I The results are indicated in Table I, with increasing numbers of plus signs indicating higher levels of RNA expression in a particular tissue. Samples which did not yield PCR amplification products were retested by using the residual 15 µl of negative PCR reactions in a reamplification reaction of 5 or 6 cycles. The results of any reamplification reactions are reported as − or (±) in Table I.

No signal was observed on amplification of genomic DNA using standard PCR conditions with primers BLE70 and BLE71 after 30 and 33 cycles with an annealing step of 60° C. Of the normal tissues analyzed, only the testis, breast, term placenta, and one out of two uterus samples were positive (Table I). Investigating the expression of LAGE-1 and NY-ESO-1 genes, it was observed that one of the uterus samples expressed a low level of LAGE-1 mRNA, but remained clearly negative for NY-ESO-1 mRNA. Moreover, the seven endometrium and two myometrium RNA samples remained negative for both genes. On the other hand, both testis samples showed LAGE-1 and NY-ESO-1 expression at a level similar to expression in LB373-MEL4.0 cells. Control amplifications were performed using β-actin specific primers. All of these cDNA samples strongly expressed β-actin as judged by the signal obtained after a PCR amplification for 21 cycles. From a panel of 6 other samples of normal tissues already typed negative with primers SL25 and BLE56, all were also found negative using LAGE-1 specific BLE72-BLE71 primers. Four of these samples, however, were found positive for NY-ESO-1 expression, but below the threshold of 1% of the expression found in LB373-MEL4.0 cells. Those normal samples which exhibited a low level of NY-ESO-1 expression are the skin, the lung, adrenals and breast (Table I).

TABLE I

Expression of genes LAGE-1 & NY-ESO-1 in normal tissues (RT-PCR)

| Tissue Sample | code | LAGE-1 or NY-ESO-1 | LAGE-1 | NY-ESO-1 |
|---|---|---|---|---|
| brain | JNO10 | − | − | − |
| retina | SH8-5 | − | − | − |
| PBL | LB33, LB569, LB678 | − | − | − |
| skin | LB243 | − | − | (±) |
| breast | LB520, LB673 | ± | − | ± |
| heart | LB1266 | − | − | − |
| muscle | CLO84033 | − | − | − |
| lung | LB175, LB264 | − | − | ± |
| bone marrow | LB214, LB1765 | − | − | − |
| liver | LB898 | − | − | − |
| kidney | BA4, BA25 | − | − | − |
| adrenal glands | LB535, LB538 | − | − | ± |
| testis | HM31, LB882 | ++/+++ | ++/+++ | ++/+++ |
| prostate | HM88, CLO64038 | − | − | − |
| ovary | LB1266, CLO84036 | − | − | − |
| term placenta | LB692, LB695 | ± | ± | ± |
| uterus | LB1022 | ± | ± | − |
| uterus | CLO64029# | − | − | − |
| endometrium d.2, 13 | LB1872, LB1874 | − | − | − |
| endometrium d.19-32 | 5 samples | − | − | − |
| myometrium | LB1031, LB1032 | − | − | − |

CLO64029: pool of 10 uterus from women (age 15-74) deceased from trauma, purchased from Clontech.

B. Tumor Samples

Total RNA of tumor samples of the origins indicated in Table II was used in RT-PCR reactions with LAGE-1 and NY-ESO-1 specific primers (BLE70 and BLE71) as described for normal tissues. Positive samples were retested by amplification using primers BLE71 and either BLE72 (specific for LAGE-1 transcript) or BLE73 (specific for NY-ESO-1 transcripts) for 30 cycles as described above with an annealing step at 62° C. for one minute and an extension step at 72° C. for 2 minutes using 0.5U DYNAZYME™ according to the manufacturer's instructions. The amount of RNA and efficiency of cDNA synthesis were controlled for by parallel PCR reactions with a set of mactin specific primers.

Since two normal uterus samples showed a basal expression of gene LAGE-1, tumor samples derived from this organ were studied further. Surprisingly, among 8 tumors tested (4 tumors of the cervix and 4 tumors of the myometrium), none appear to be positive for LAGE-1 or NY-ESO-1 with primers BLE70-BLE71 after 30 and 33 cycles, in spite of a confirmed good β-actin expression (Table II). Expression of LAGE-1 in uterus was further verified using a commercial RNA sample, derived from uterine tissues from 10 normal women deceased by trauma, which tested negative for both genes in spite of a good actin expression.

As indicated in Table II, no expression of LAGE-1 or NY-ESO-1 genes was detected in colon, kidney, thyroid and brain cancers, nor in leukemias, as assessed by RT-PCR with primers BLE70-BLE71. Expression of LAGE-1 or NY-ESO-1 genes in breast cancer was not rare, but was faint. The expression in melanomas, SCLC, sarcomas, head and neck, prostate and bladder tumors was stronger, relatively more frequent and correlated with the expression of other genes known to encode antigenic peptides as shown in Table III. The same cDNA samples were tested for expression of a panel of TRAPs including MAGE-1, -2, -3, -4, -6 and -12, BAGE, PRAME, GAGE-1&2, -3, -4, -5 and -6, and RAGE. A correlation of the expression of LAGE-1 or NY-ESO-1 with activation of MAGE-1 or other TRAPS is given in Table III. Half of the samples that were positive for LAGE-1 were also positive for MAGE-A1 whereas only twelve percent of the negative samples expressed MAGE-A1. A similar correlation of expression was found between LAGE-1 and MAGE-A3.

Because the expression of LAGE-1 was clearly correlated with that of the MAGE genes, which are activated in tumors upon demethylation of the promoter region, studies were carried out to determine if demethlyation could also induce LAGE-1 expression. Phytohemagglutinin-stimulated lymphoblastoid cells or tumor cells that were negative for LAGE-1 and NY-ESO-1 turned out to express these genes after treatment by deoxyazacytidine, indicating that methylation is involved in the control of both genes. In confirmation, it was observed that HpaII sites located in exon 1 and in the promoter of LAGE-1 were methylated in blood mononucleated cells and in tumor cell lines that did not express LAGE-1 , whereas the HpaII sites were demethylated in tumor cell lines that expressed LAGE-1

LAGE-1 and NY-ESO-1 each accounted for 75% of positive tumor samples. Thus, as demonstrated in Table II both LAGE-1 and NY-ESO-1 family genes were expressed independently of each other. Sarcomas of various histological types preferentially expressed high levels of NY-ESO-1 RNA, independent of the expression of known tumor associated antigens encoding genes.

Using the cDNAs of eight samples which express LAGE-1 and NY-ESO-1 genes simultaneously or NY-ESO-1 alone as templates for RT-PCR reactions, NY-ESO-1 sequence was amplified with primers BLE73 and BLE71 for use as starting material in sequencing reactions. Primer BLE56 (SEQ ID NO:3) was used to prime sequencing reactions. A unique sequence that was identical to the corresponding region of clone 3 derived from LB373-MEL4.0 cells was observed, demonstrating both the specificity of the PCR reactions and the absence of polymorphism in this region of the NY-ESO-1 gene (see FIG. 1).

TABLE II

Expression of genes LAGE-1 & NY-ESO-1 in tumors (RT-PCR)

| Sample | Number | LAGE-1 & NY-ESO-1 Positive BLE70-BLE71 | (%) | LAGE-1 BLE72-BLE71 | NY-ESO-1 BLE73-BLE71 |
|---|---|---|---|---|---|
| COLON | 9 | 0 | | ND | ND |
| LEUKEMIA | 17 | 0 | 0% | ND | ND |
| B-LYMPHOMA | 6 | 1 | | 1 | 1 |
| MELANOMA | 21 | 7 | 33% | 6 | 5 |
| HEAD & NECK | 15 | 4 | 27% | 4 | 3 |
| LUNG | 15 | 5 | 33% | 5 | 3 |
| KIDNEY | 10 | 0 | | ND | ND |
| SARCOMA | 19 | 9 | 47% | 4/8 | 6 |
| BREAST | 12 | 4 | | 2 | 3 |
| UTERUS | 8 | 0 | | 0 | 0 |
| cervix | | 0/4 | | | |
| corpus | | 0/4 | | | |
| BLADDER | 15 | 5 | 33% | 4 | 5 |
| BRAIN | 4 | 0 | | ND | ND |
| THYROID | 3 | 0 | | ND | ND |
| PROSTATE | 12 | 4 | | 3 | 3 |
| | | | | | |
| TOTAL | 166 | | | | |
| Positive | | 39 | | 29/38 | 29/39 |
| Positive (%) | | | 23% | 76% | 74% |

TABLE III

Expression of LAGE-1 & NY-ESO-1 genes by RT-PCR using BLE70-BLE71 (30 cycles)

| | | | | among tumor samples | | |
|---|---|---|---|---|---|---|
| Sample | Number | Positive | (%) | MAGE-1 pos. | ≧1 other TRAP pos. (MAGE-1 neg.) | TRAPs neg. |
| COLONS | 9 | 0 | | — | 0/5 | 0/4 |
| LEUKEMIAS | 17 | 0 | 0% | 0/1 | 0/9 | 0/7 |
| B-LYMPHOMAS | 6 | 1 | | — | 1/3 | 0/3 |
| MELANOMAS | 21 | 7 | 33% | 3/5 | 4/9 | 0/7 |
| HEAD & NECK | 15 | 4 | 27% | 3/4 | 1/6 | 0/5 |
| LUNG | 15 | 5 | 33% | 3/5 | 2/5 | 0/5 |
| nsclc (AC) | | 3/8 | | 2/4 | 1/2 | 0/2 |
| nsclc (epid.) | | 1/6 | | — | 1/3 | 0/3 |
| other | | 1/1 | | 1/1 | — | — |
| KIDNEY | 10 | 0 | | 0/2 | 0/2 | 0/6 |
| SARCOMAS | 19 | 9 | 47% | 2/2 | 4/8 | 3/9 |
| BREAST | 12 | 4 | 33% | 2±/5 | 2±/3 | 0/4 |
| UTERUS | 8 | 0 | | — | 0/3 | 0/5 |
| cervix | | 0/4 | | — | 0/2 | 0/2 |
| corpus (benign) | | 0/4 | | — | 0/1 | 0/3 |
| BLADDER | 15 | 5 | 33% | 3/4 | 1/5 | 1/6 |
| BRAIN | 4 | 0 | | — | 0/2 | 0/2 |
| THYROID | 3 | 0 | | — | 0/2 | 0/1 |
| PROSTATE | 12 | 4 | 33% | 1/3 | 1/1 | 2/8 |
| | | | | | | |
| TOTAL | 166 | | | 31 | 63 | 72 |
| % of all samples | | | | 19% | 38% | 43% |
| Positive | | 39 | | 17 | 16 | 6 |
| Positive (%) | | | 23% | 53% | 23% | 11% |

Example 4

Northern Blot on Total RNA

Various tumor cell lines and samples positive for LAGE-1 and/or NY-ESO-1 by RT-PCR with primers BLE70-BLE71 were assayed by Northern blotting in order to determine the length of the messenger RNA. A normal lung sample was used as a negative control.

Total RNA (10 µg) from normal testis, normal and tumoral lung from the same patient (LB264), from two melanoma cell lines (LB373 and LB24) and one sarcoma cell line (LB188) were separated by electrophoresis in a denaturing 1.3% agarose gel, blotted overnight against Hybond C filters (Amersham), using the turbo-blotting system from Schleicher & Schuell (Keene, N.H.). RNA was fixed on the filter by UV autocrosslinking at 254 nm (Stratalinker, Stratagene, La Jolla, Calif.), and hybridized with $5 \times 10^6$ CPM of a PCR probe of 842 base pairs in a 5 ml Dextran sulfate/SDS/NaCl solution. The probe was obtained by amplification of LAGE-1 clone 2 with primers BLE70 and BLE71 in the presence of labeled dCTP. Specific activity of the probe was determined after purification by Chromaspin X (Clontech, Palo Alto, Calif.). After overnight hybridization at 60° C., the filter was washed in successive baths of 2×SSC at increasing temperatures up to 60° C. The washed filter was exposed to X-ray film to visualize the hybridization signal as an autoradiogram.

Two clear signals of approximately 750 and 1000 nucleotides in length were observed on the autoradiogram. These sizes are in good agreement with the length of cDNA clones 2, 3, and 4 which are about 993, 744, and 746 nucleotides respectively, without the poly-A tail. Accordingly, the cDNAs of LAGE-1b (clone 2), NY-ESO-1 clone 3, and LAGE-1 a (clone 4) are believed to be nearly complete. The completeness of the cDNAs was further assessed by RT-PCR results obtained with various upstream sense primers and antisense primer located in exon 1 (see Example 5). These signals were barely visible for the testis, and absent for the normal lung sample. Ethidium bromide staining revealed no significant quantitative difference between the six samples, and the 28S rRNA was undegraded in all samples.

Example 5

Gene Structure and Chromosome Mapping

Genomic structure with three exons was already suggested for LAGE-1 and NY-ESO-1 by sequencing cloned PCR products that were obtained from genomic DNA of allogeneous normal lymphocytes by amplification with primer pair BLE70-BLE71. However, no information could be retrieved outside these primers. Particularly, the promoter region remained undefined with this preliminary analysis.

A library constructed with the genomic DNA of the melanoma cell line LB33-MELA and divided in groups of $3 \times 10^4$ to $9 \times 10^4$ cosmids was used for isolation of the entire LAGE-1 gene. Bacteria of 12 groups were submitted to amplification with primer pair BLE72-BLE71 that is specific for LAGE-1. A positive group was chosen for its low diversity ($3 \times 10^4$ independent clones). Bacteria ($1.6 \times 10^5$) of this group were spread on 4 filters. The filters were screened with a labeled PCR product obtained from genomic DNA with primers BLE70-BLE71. Hybridization buffer (10 ml) contained 3.5× SSC, 1× Denhardt, 0.5% SDS, EDTA (2 mM), Na$_2$PO$_4$ (25 mM) and salmon sperm DNA (100 µg/ml). Filters were hybridized overnight at 65° C. in rotating cylinders. They were washed twice in 500 ml of 2×SSC, 0.5% SDS, at 60° C. for 15 min. and twice in 500 ml of 0.2×SSC, 0.1% SDS at 65° C. for 10 min. One cosmid was isolated. A digestion of the cosmid with various restriction enzymes was fractionated by electrophoresis, blotted and hybridized with the same PCR probe. Hybridizing fragments were compared to the data obtained from a Southern blot of genomic DNA previously probed with a PCR product derived from cDNA clone 2 and amplified with primers BLE70-BLE71. Comparison of restriction fragments and hybridizing bands indicated that the isolated cosmid did contain the LAGE-1 gene. Relevant signals were obtained with EcoRI (4.5 kb), BamHI (4.8 kb, 1 kb, and 0.2 kb) and PstI (0.8 kb, 0.7 kb and 0.5 kb). Sequences were determined by direct sequencing of the cosmid with specific primers and by sequencing various sub-clones. The sequences of the LAGE-1 nucleic acids have been deposited in the EMBL database under accession numbers AJ223093 (LAGE-1 gene), AJ223040 (LAGE-1b cDNA [clone 2]), AJ223041 (LAGE-1a cDNA [clone 4]) and AJ003149 (NY-ESO-1 [clone 3]).

As indicated by the sizes of the bands observed on Northern blots, the transcription start appears to be located very near the 5' ends of the cDNA clones shown in FIG. 1. Moreover, RT-PCR experiments with a specific antisense primer located in exon 1 and various sense primers located upstream of the 5' end of LAGE-1 clone 2 indicated that about 90% of the transcripts start between positions −25 and +1, whereas the other transcripts start between positions −100 and −25. The LAGE-1 promoter sequence apparently does not contain a TATA box but does contain two Sp1 sites at positions −24 and −145 and a consensus core Ets site (aggat) at position −51. A CpG island is located between positions −400 and +333. It displays 73% of G+C, with a frequency of CpG dinucleotide corresponding to 0.6 of that expected on a random basis (Gardiner-Garden and Frommer, *J. Mol. Biol.* 96:261-282, 1987).

In cell line LB373-MEL, intron 2 is spliced out in only half the transcripts. A high frequency of partially spliced LAGE-1 mRNA is also observed in tumor cell lines and surgical tumor samples as shown by Northern blotting analysis. The presence of two forms of LAGE-1 mRNA was confirmed by RT-PCR experiments. The partially spliced LAGE-1 mRNA contains an open reading frame encompassing intron 2 almost completely and coding for a protein of 210 amino acids, whereas the fully spliced mRNA codes for a polypeptide of 180 amino acids. The protein encoded by the partially spliced mRNA may therefore have a function that is different than the protein encoded by the fully spliced mRNA.

The cDNA and cosmid sequences derived from different patients enabled detection of polymorphisms (non-exhaustive) in the LAGE-1 gene. Two base substitutions were observed in the coding sequences of exon 1 resulting in two amino acid changes (Gln to Arg for residue 6 and Gln to Glu for residue 89). A third substitution observed in exon 2 is silent (Pro at residue 115). A fourth polymorphism was observed eight nucleotides downstream of the 5' splice site of intron 2, thus modifying residue 138 from Arg to Trp in the partially spliced LAGE-1 polypeptide.

It was verified that the cosmid respected the gene structure. In order to verify the sequences of the promoter as found in the cosmid, primers were designed to amplify the 5' flanking sequence of the gene using genomic DNA as a template. Various pairs of primers produced signals of identical size in the cosmid and in genomic DNA. The largest PCR product was tested by hybridization with an internal oligonucleotide (BLE70) giving a unique band of identical size in cosmid and genomic DNA.

Chromosome mapping of gene LAGE-1 was performed in two steps. First, monochromosomal somatic hybrids provided by the UK HGMP resource center (batch 96/01) containing human-mouse and human-hamster hybrid cells permitted the location of genes LAGE-1 (LL-1.1) and NY-ESO-1 (LL-1.2) to a distal region of chromosome Xq. PCR amplification using the gene-specific primer pairs BLE72-BLE71 and BLE73-BLE71 (for LAGE-1 and NY-ESO-1, respectively) was performed. Specific LAGE-1 and NY-ESO-1 PCR signals were observed with hybrids harboring the entire human X chromosome or a distal Xq fragment. Second, the chromosome mapping of LAGE-1 was then refined by fluorescence in situ hybridization (FISH) experiments performed on metaphase spreads of normal lymphocytes (PBL) stimulated with phytohemagglutinin (PHA) to Xq28. Since a 320 kb pseudoautosomal telomeric region was described in this region (Kvaloy et al., *Hum. Mol. Genet.* 3:771-778, 1994), the experiment was repeated using the PHA-stimulated PBL of a male donor: chromosome Y remained negative.

Chromosomes were identified by simultaneous G banding analysis using DAPI counter staining. The X chromosome was identified by cohybridization with pBAM X.5, a plasmid probe kindly given by Dr. Hans Dauwerse (Leiden, The Netherlands) which recognizes DXZ1, the alpha satellite specific for the X chromosome centromere. Slides were viewed with a Leitz DMRB fluorescence microscope (E. Leitz Inc., Wetzlar, Germany) equipped with a cooled CCD camera (Photometrics, Tucson, Ariz.) run by Vysis software (Vysis, Stuttgart, Germany). At least ten metaphase spreads were evaluated in each experiment.

Because the MAGE-A genes also map to Xq28, LAGE-1 was mapped relative to the MAGE-A genes. A cosmid carrying the MAGE-A6 and MAGE-A2 genes (Rogner et al., *Genomics* 29: 725-731, 1995) was used as a co-hybridizing probe. The LAGE-1 signal was superimposed to the MAGE signal suggesting that both genes lie within 2 Mb in the Xq28 band.

Example 6

Features of the LAGE-1 Protein

The 180 amino acid proteins encoded by the LAGE-1 a cDNA (clone 4) and the NY-ESO-1 cDNA display 84% identity and, taking into account conservative changes, 89% homology. The LAGE-1 and NY-ESO-1 proteins have isoelectric points of 10.9 and 8.5, respectively. Four regions of 45 amino acids can be distinguished in the LAGE-1 polypeptide. The first two regions are encoded by exon 1 and are very rich in glycine residues (42% and 22%), which frequently occur as doublets. The first region is acidic whereas the second is highly basic. The third region, encoded by exon 2, supports a major difference between the two genes, being basic in LAGE-1 (iso-electric point of 10.0) and acidic in NY-ESO-1 (iso-electric point of 4.6). The fourth region, encoded by exon 3, is basic and contains a hydrophobic stretch near the C-terminus. The LAGE-1b polypeptide of 210 amino acids (clone 2) lacks the hydrophobic stretch. The three polypeptides display several putative phosphorylation sites for casein kinase II, which is known to phosphorylate many substrates involved in the control of cell division (Allende and Allende, *FASEB J.* 9: 313-323, 1995).

Example 7

Identification of the Portion of LAGE-1 Encoding a Tumor Rejection Antigen

On the basis of the findings made with the MAGE genes (and other genes) wherein antigenic peptides are formed from the protein products of the gene, it is believed that tumor cells expressing LAGE-1 carry at least one antigen that can be recognized by autologous cytolytic T lymphocytes (CTL) in the form of LAGE-1 encoded antigenic peptides presented by various HLA molecules. An analysis of LAGE-1 expression indicated that the number of LAGE-1 molecules present in LB373-MEL cells is similar to that of MAGE-A1 mRNAs in melanoma cell line MZ2-MEL. It has been shown that cell lines that express MAGE-A1 mRNA levels above 10% of that found in MZ2-MEL cells are recognized by anti-MAGE CTL (Lethé et al., *Melanoma Research* 7:S83-S88, 1997). On this basis, it is believed that half of the LAGE-1 positive tumors express enough antigen to be targets for immunotherapy.

At least two experimental approaches can be taken to identify antigens encoded by LAGE-1. In a first method, CTL clones are generated by stimulating the peripheral blood lymphocytes (PBLs) of a patient with autologous normal cells transfected with DNA clones encoding LAGE-1a or LAGE-1b polypeptides (e.g. SEQ ID NOs: 6 and 4) or with irradiated PBLs loaded with synthetic peptides corresponding to the putative proteins and matching the consensus for the appropriate HLA class I molecule to localize antigenic peptides within the LAGE-1 polypeptides (see, e.g., van der Bruggen et al., *Eur. J. Immunol.* 24:3038-3043, 1994; MAGE3 peptides presented by HLA.A2; Herman et al., *Immunogenetics* 43:377-383, 1996). Localization of one or more antigenic peptides in a protein sequence can be aided by HLA peptide binding predictions made according to established rules for binding potential (e.g., Parker et al, *J. Immunol.* 152:163, 1994; Rammensee et al., *Immunogenetics* 41:178-228, 1995). HLA binding predictions can conveniently be made using an algorithm available via the Internet on the National Institutes of Health World Wide Web site at URL bimas.dcrt.nih.gov.

Alternatively, CTL clones obtained by stimulation of lymphocytes with autologous tumor cells shown to express one or both of the LAGE-1 clones are screened for specificity against COS cells transfected with LAGE-1 cDNAs and autologous HLA alleles as described by Brichard et al. (*Eur. J Immunol.* 26:224-230, 1996).

CTL recognition of LAGE-1 is determined by measuring release of TNF from the cytolytic T lymphocyte or by $^{51}$Cr release assay (Herin et al., *Int. J. Cancer* 39:390-396, 1987). If a CTL clone specifically recognizes a transfected COS cell, shorter fragments of the coding sequences are tested to identify the region of the gene that encodes the peptide. Fragments of LAGE-1 are prepared by exonuclease III digestion or other standard molecular biology methods. Synthetic peptides are prepared to confirm the exact sequence of the antigen.

Optionally, shorter fragments of LAGE-1 cDNAs are generated by PCR. Shorter fragments are used to provoke TNF release or $^{51}$Cr release as above.

Synthetic peptides corresponding to portions of the shortest fragment of a LAGE-1 clone which provokes TNF release are prepared. Progressively shorter peptides are synthesized to determine the optimal LAGE-1 tumor rejection antigen peptides for a given HLA molecule.

Other aspects of the invention will be clear to the skilled artisan and need not be repeated here. All patents, published patent applications and literature cited herein are incorporated by reference in their entirety.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. An isolated polypeptide comprising the amino acid sequence set forth as SEQ ID NO:5.

2. A composition comprising the isolated polypeptide of claim 1.

3. The composition of claim 2, further comprising a pharmaceutically acceptable carrier.

4. An isolated polypeptide consisting of an immunogenic fragment of SEQ ID NO:5, wherein the immunogenic fragment is 8 or more amino acids, and wherein the immunogenic fragment of 8 or more amino acids is not identical to a fragment of 8 or more amino acids of SEQ ID NO:9.

5. A composition comprising the isolated polypeptide of claim 4.

6. The composition of claim 5, further comprising a pharmaceutically acceptable carrier.

* * * * *

UNITED STATES PATENT AND TRADEMARK OFFICE
CERTIFICATE OF CORRECTION

PATENT NO. : 7,563,870 B2                                       Page 1 of 1
APPLICATION NO. : 10/877373
DATED : July 21, 2009
INVENTOR(S) : Lethe et al.

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 287 days.

Delete the phrase "by 287 days" and insert -- by 484 days --

Signed and Sealed this

Thirteenth Day of April, 2010

David J. Kappos
*Director of the United States Patent and Trademark Office*